(12) United States Patent
Meijer et al.

(10) Patent No.: US 12,306,535 B2
(45) Date of Patent: May 20, 2025

(54) PHOTOACID GENERATOR FOR CHEMICALLY AMPLIFIED PHOTORESISTS FOR DEEP ULTRA VIOLET AND EXTREME ULTRAVIOLET LITHOGRAPHY

(71) Applicant: International Business Machines Corporation, Armonk, NY (US)

(72) Inventors: Gerhard Ingmar Meijer, Zurich (CH); Valery Weber, Gattikon (CH); Peter Willem Jan Staar, Zurich (CH)

(73) Assignee: International Business Machines Corporation, Armonk, NY (US)

( * ) Notice: Subject to any disclaimer, the term of this patent is extended or adjusted under 35 U.S.C. 154(b) by 586 days.

(21) Appl. No.: 17/648,495

(22) Filed: Jan. 20, 2022

(65) Prior Publication Data

US 2023/0229077 A1    Jul. 20, 2023

(51) Int. Cl.
*G03F 7/004* (2006.01)
*C07C 381/12* (2006.01)
(Continued)

(52) U.S. Cl.
CPC .......... *G03F 7/0045* (2013.01); *C07C 381/12* (2013.01); *C07F 5/027* (2013.01); *G03F 7/0382* (2013.01); *G03F 7/0392* (2013.01)

(58) Field of Classification Search
None
See application file for complete search history.

(56) References Cited

U.S. PATENT DOCUMENTS 7,192,686 B2 *  3/2007  Meagley ............... G03F 7/0045
                                                      430/326
8,034,533 B2    10/2011  Liu et al.
(Continued)

FOREIGN PATENT DOCUMENTS

EP    2998297 A1    3/2016

OTHER PUBLICATIONS

Zhou "Constructing organic superacids from superhalogens is a rational route as verified by DFT calculations" Phys. Chem. Chem. Phys. 2019, 21, 2804 (Year: 2019).*
(Continued)

*Primary Examiner* — Mark F. Huff
*Assistant Examiner* — Kevin J Drummey
(74) *Attorney, Agent, or Firm* — Kelsey Skodje

(57) ABSTRACT

A photoacid generator (PAG) anion, a photoresist composition, and a method are disclosed. The PAG anion includes a moiety, selected from an alkyl group, a monocyclic aromatic group, and a bicyclic aromatic group, that includes a carbon atom with a negative elementary charge. The PAG anion also includes an electron acceptor atom, selected from boron(III), aluminum(III), and phosphorus(V), which is covalently bonded to the carbon atom. The PAG anion also has at least one electron-withdrawing R group. The photoresist composition has a PAG that includes the PAG anion and a cation selected from triphenylsulfonium, diphenyliodonium, phenylthiolanium, and derivatives thereof. The method includes forming a layer of the photoresist composition over a material surface on a substrate, irradiating the layer to form a pattern of radiation-exposed regions, selectively removing portions of the irradiated layer to form exposed portions of the material surface, and etching or ion implanting the exposed portions.

20 Claims, 16 Drawing Sheets triphenylsulfonium 1,2,3,4,5,6,7,8-octacyano-benzo[a]borinine

UV light ↓

1,2,3,4,5,6,7,8-octacyano-4aH-benzo[a]borinine

(51) Int. Cl.
  *C07F 5/02*     (2006.01)
  *G03F 7/038*    (2006.01)
  *G03F 7/039*    (2006.01)

(56) References Cited

U.S. PATENT DOCUMENTS

| | | |
|---|---|---|
| 8,039,194 B2 | 10/2011 | Glodde |
| 8,343,706 B2 | 1/2013 | Liu et al. |
| 11,846,886 B2 | 12/2023 | Meijer et al. |
| 2003/0134227 A1 | 7/2003 | Cameron et al. |
| 2019/0243243 A1* | 8/2019 | Naito .............. G03F 7/004 |

OTHER PUBLICATIONS

Leito, "Anions N(C(CN)2)3- and P(C(CN)2)3- and the superacidic properties of their conjugate acids", Journal of Molecular Structure: THEOCHEM 815 (2007) 41-43. (Year: 2007).*

Asakura et al., "Novel photoacid generators for chemically amplified resists with g-line, i-line and DUV exposure," https://www.spiedigitallibrary.org/conference-proceedings-of-spie/4345/0000/Novel-photoacid-generators-for-chemically-amplified-resists-with-g-line/10.1117/12.436880.short?SSO=1, 10 pgs., Aug. 2001.

Liu et al., "Design, Synthesis and Characterization of Fluorine-free PAGs for 193 nm Lithography," https://www.spiedigitallibrary.org/conference-proceedings-of-spie/7639/1/Design-synthesis-and-characterization-of-fluorine-free-PAGs-for-193/10.1117/12.846600.short?SSO=1, 8 pgs. Mar. 2010.

* cited by examiner 4A     4B     4C     4D 4E     4F     4G     4H 4I     4J     4K     4L 4M     4N     4O     4P

PHOTOACID GENERATOR FOR CHEMICALLY AMPLIFIED PHOTORESISTS FOR DEEP ULTRA VIOLET AND EXTREME ULTRAVIOLET LITHOGRAPHY

BACKGROUND

The present disclosure relates to a conjugate base of a superacid and, more specifically, to a photoacid generator anion for a photoacid generator (PAG) for chemically amplified photoresists for deep ultraviolet (DUV) or extreme ultraviolet (EUV) lithography.

Various types of lithography are used for semiconductor manufacturing of next generation devices. Photolithography can, using controlled light, define a pattern in a thin photosensitive polymer layer (photoresist) such that the resulting polymer pattern can be transferred into or onto an underlying substrate by etching, deposition, or implantation. Different wavelengths of light can be used. For example, DUV lithography can use 193 nm or 248 nm light, corresponding to an energy of about 6 eV or 5 eV, respectively. EUV lithography can use about 13.5 nm light, which corresponds to an energy of about 92 eV.

SUMMARY

Various embodiments are directed to a composition that includes a photoacid generator (PAG) anion. The PAG anion includes a first moiety selected from an alkyl group, a monocyclic aromatic group, and a bicyclic aromatic group. The first moiety has a carbon atom with a negative elementary charge. The PAG anion also includes an electron acceptor atom selected from boron(III), aluminum(III), and phosphorus(V). The electron acceptor atom is covalently bonded to the carbon atom. The PAG anion also has R groups that include at least one electron-withdrawing R group. In some embodiments, the PAG anion has the general formula (I):

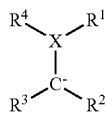
(I)

where X represents the electron acceptor atom, and R1, R2, R3, and R4 represent the R groups. In other embodiments, the PAG anion has the general formula (II):

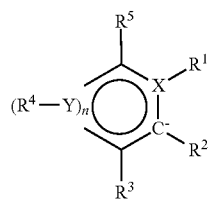
(II)

where X represents the electron acceptor atom, R1, R2, R3, R4, and R5 represent the R groups, Y represents a methylene group, and n is 0 or an integer in a range from 1 to 3. In further embodiments, the PAG anion has the general formula (III):

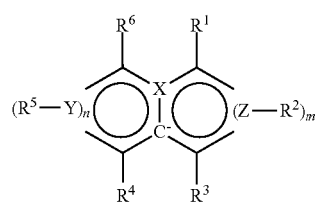
(III)

where X represents the electron acceptor atom, R1, R2, R3, R4, R5, and R6 represent the R groups, Y and Z each represent a methylene group, n is 0 or an integer in a range from 1 to 3, and m is 0 or an integer in a range from 1 to 3. In some embodiments, at least two adjacent R groups in formulas (II) and/or (III) are linked with each other to form a five-, six-, or seven-membered aromatic ring that includes at least one electron-withdrawing group. Examples of electron-withdrawing R groups can include cyano, cyanoimino, linear or branched $C_1$ to $C_4$ cyanoalkyl, linear or branched $C_1$ to $C_4$ cyanoalkenyl, linear or branched $C_1$ to $C_4$ cyanoalkylene, $C_1$ to $C_4$ alkylsulfonyl, ($C_1$ to $C_4$ alkylsulfonyl)imino, linear or branched $C_1$ to $C_4$ ($C_1$ to $C_4$ alkylsulfonyl) alkyl, linear or branched $C_1$ to $C_4$ ($C_1$ to $C_4$ alkylsulfonyl) alkenyl, linear or branched $C_1$ to $C_4$ ($C_1$ to $C_4$ alkylsulfonyl) alkylene, fluoro, fluoroimino, linear or branched $C_1$ to $C_8$ fluoroalkyl, (linear or branched $C_1$ to $C_8$ fluoroalkyl)imino, linear or branched $C_1$ to $C_8$ fluoroalkenyl, linear or branched $C_1$ to $C_8$ fluoroalkylene, ($C_1$ to $C_4$ fluoroalkyl)sulfonyl, ($C_1$ to $C_4$ fluoroalkyl)sulfonylimino, linear or branched $C_1$ to $C_4$ ($C_1$ to $C_4$ fluoroalkyl)sulfonylalkyl, linear or branched $C_1$ to $C_4$ ($C_1$ to $C_4$ fluoroalkyl)sulfonylalkenyl, linear or branched $C_1$ to $C_4$ ($C_1$ to $C_4$ fluoroalkyl)sulfonylalkylene, $C_3$ to $C_7$ fluorocycloalkyl, ($C_3$ to $C_7$ fluorocycloalkyl)imino, $C_5$ to $C_7$ fluoroaryl, ($C_5$ to $C_7$ fluoroaryl)imino, and derivatives thereof. In some embodiments, an electron-withdrawing R group can be a trialkylstannyl-, a triarylstannyl-, a dialkylantimonyl-, a diarylantimonyl-, a dialkylbismuthyl-, or a diarylbismuthyl group. Further examples of electron-withdrawing R groups can include cyanoethenyl, dicyanoethenyl, tricyanoethenyl, methylsulfonyl, methylsulfonylimino, cyanomethylene, dicyanomethylene, methylsulfonylmethylene, and bis(methylsulfonyl)methylene. The R groups can also include at least one non-electron-withdrawing group (e.g., H, optionally substituted linear or branched alkyl, optionally substituted cycloalkyl, optionally substituted aryl, optionally substituted saturated or unsaturated heterocyclic group, or derivatives thereof). The PAG anion can be selected from 2-(dicyanoboranyl)propanedinitrile anion, bis(methylsulfonyl)boranyl-bis(methylsulfonyl)methane anion, dicyanoboranyl-bis(methylsulfonyl)methane anion, 2-(bis(trifluoromethyl)boranyl)-1,1,1,3,3,3-hexafluoropropane anion, bis(trifluoromethylsulfonyl)boranyl-bis(trifluoromethylsulfonyl)methane anion, dicyanoboranyl-bis(trifluoromethylsulfonyl)methane anion, 2-(dicyanoaluminyl)propanedinitrile anion, bis(methylsulfonyl)aluminyl-bis(methylsulfonylmethane) anion, dicyanoaluminyl-bis(methylsulfonylmethane) anion, 2-(bis(trifluoromethyl)aluminyl)-1,1,1,3,3,3-hexafluoropropane anion, bis(trifluoromethylsulfonyl)aluminyl-bis(trifluoromethylsulfonyl)methane anion, dicyanoaluminyl-bis(trifluoromethylsulfonyl)methane anion, bis(cyanoimino)(dicyanomethyl)phosphorane anion, bis(methylsulfonylimino)-bis(methylsulfonyl)(methylsulfonyl)methylphosphorane anion, bis(trifluoromethylimino)(1,1,1,3,3,3-hexafluoroprop-2-yl)phosphorane anion, bis (trifluoromethylsulfonylimino)-bis(trifluoromethylsulfonyl)methylphosphorane anion, bis(dicyanomethylene)(dicyanomethyl)phosphorane anion, bis(bis(methylsulfonyl)methylene)-bis(methylsulfonyl)methylphosphorane anion, bis(bis(trifluoromethyl)methylene)(1,1,1,3,3,3-hexafluoroprop-2-yl)phosphorane anion, bis(bis(trifluoromethylsulfonyl)methylene)-bis(trifluoromethylsulfonyl)methylphosphorane anion, 1,2,3,4,5,6-hexacyanoborinine anion, 1,2,3,4,5,6-hexakis(methylsulfonyl)borinine anion, 1-cyano-2,3,4,5,6-pentakis(methylsulfonyl)borinine anion, 1,2,3,4,5,6-hexakis(trifluoromethyl)borinine anion, 1,2,3,4,5,6-hexakis(trifluoromethylsulfonyl)borinine anion, 1-cyano-2,3,4,5,6-pentakis(trifluoromethylsulfonyl)borinine anion, 1,2,3,4,5,6-hexacyanoaluminine anion, 1,2,3,4,5,6-hexakis(methylsulfonyl)aluminine anion, 1-cyano-2,3,4,5,6-pentakis(methylsulfonyl)aluminine anion, 1,2,3,4,5,6-hexakis(trifluoromethyl)aluminine anion, 1,2,3,4,5,6-hexakis(trifluoromethylsulfonyl)aluminine anion, 1-cyano-2,3,4,5,6-pentakis(trifluoromethylsulfonyl)aluminine anion, 1,2,3,4,5,6,7,8-octacyanobenzo[a]borinine anion, 1,8-(1,2,3,4-tetracyanobuta[1,3]dieno)-2,3,4,5,6,7-hexacyanobenzo[a]borinine anion, bis-[1,8:4,5]-(1,2,3,4-tetracyanobuta[1,3]dieno)-2,3,6,7-tetracyanobenzo[a]borinine anion, 1,2,3,4,5,6,7,8-octacyanobenzo[a]aluminine anion, 1,8-(1,2,3,4-tetracyanobuta[1,3]dieno)-2,3,4,5,6,7-hexacyanobenzo[a]aluminine anion, bis-[1,8:4,5]-(1,2,3,4-tetracyanobuta[1,3]dieno)-2,3,6,7-tetracyanobenzo[a]aluminine anion, 1,2,3,4,5,6-hexakis(methylsulfonyl)borinine anion, 1-cyano-2,3,4,5,6-pentakis(methylsulfonyl)borinine anion, 1,2,3,4,5,6,7,8-octakis(methylsulfonyl)benzo[a]borinine anion, 1,2,3,4,5,6-hexakis(methylsulfonyl)aluminine anion, 1-cyano-2,3,4,5,6-pentakis(methylsulfonyl)aluminine anion, and 1,2,3,4,5,6,7,8-octakis(methylsulfonyl)benzo[a]aluminine anion. A conjugate acid of the PAG anion can have a proton dissociation energy smaller than 255 kcal/mol.

Additional embodiments are directed to a photoresist composition that includes a photoacid generator (PAG) with a PAG anion that includes a first moiety selected from an alkyl group, a monocyclic aromatic group, and a bicyclic aromatic group. The first moiety has a carbon atom with a negative elementary charge. The PAG anion also includes an electron acceptor atom selected from boron(III), aluminum (III), and phosphorus(V). The electron acceptor atom is covalently bonded to the carbon atom. The PAG anion also has R groups that include at least one electron-withdrawing R group. The PAG also includes a cation selected from triphenylsulfonium, diphenyliodonium, phenylthiolanium, and derivatives thereof. In some embodiments, the PAG is in an amount of 5 to 95% by weight, 10 to 80% by weight, or 10 to 50% by weight. A conjugate acid of the PAG anion can have a proton dissociation energy smaller than 255 kcal/mol.

Further embodiments are directed to a method of forming a patterned material feature on a substrate. A material surface is provided on the substrate. A layer of photoresist composition is formed over the surface. The photoresist composition includes a photoacid generator (PAG) with a PAG anion that includes a first moiety selected from an alkyl group, a monocyclic aromatic group, and a bicyclic aromatic group. The first moiety has a carbon atom with a negative elementary charge. The PAG anion also includes an electron acceptor atom selected from boron(III), aluminum(III), and phosphorus(V). The electron acceptor atom is covalently bonded to the carbon atom. The PAG anion also has R groups that include at least one electron-withdrawing R group. The PAG also includes a cation selected from triphenylsulfonium, diphenyliodonium, phenylthiolanium, and derivatives thereof. The method further includes irradiating the photoresist layer with an energy ray to form a pattern of radiation-exposed regions in the photoresist layer, selectively removing portions of the irradiated photoresist layer to form exposed portions of the material surface, and etching or ion implanting the exposed portions of the material surface, thereby forming the patterned material feature. The energy ray can be a deep ultraviolet (DUV) irradiation or an extreme ultraviolet (EUV) irradiation. In some embodiments, the PAG is in an amount of 5 to 95% by weight, 10 to 80% by weight, or 10 to 50% by weight.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

FIG. 5 illustrates chemical structure diagrams of acids that can be generated, upon UV exposure, by the PAG anions illustrated in FIG. 4, according to some embodiments of the present disclosure.

Figure 1:
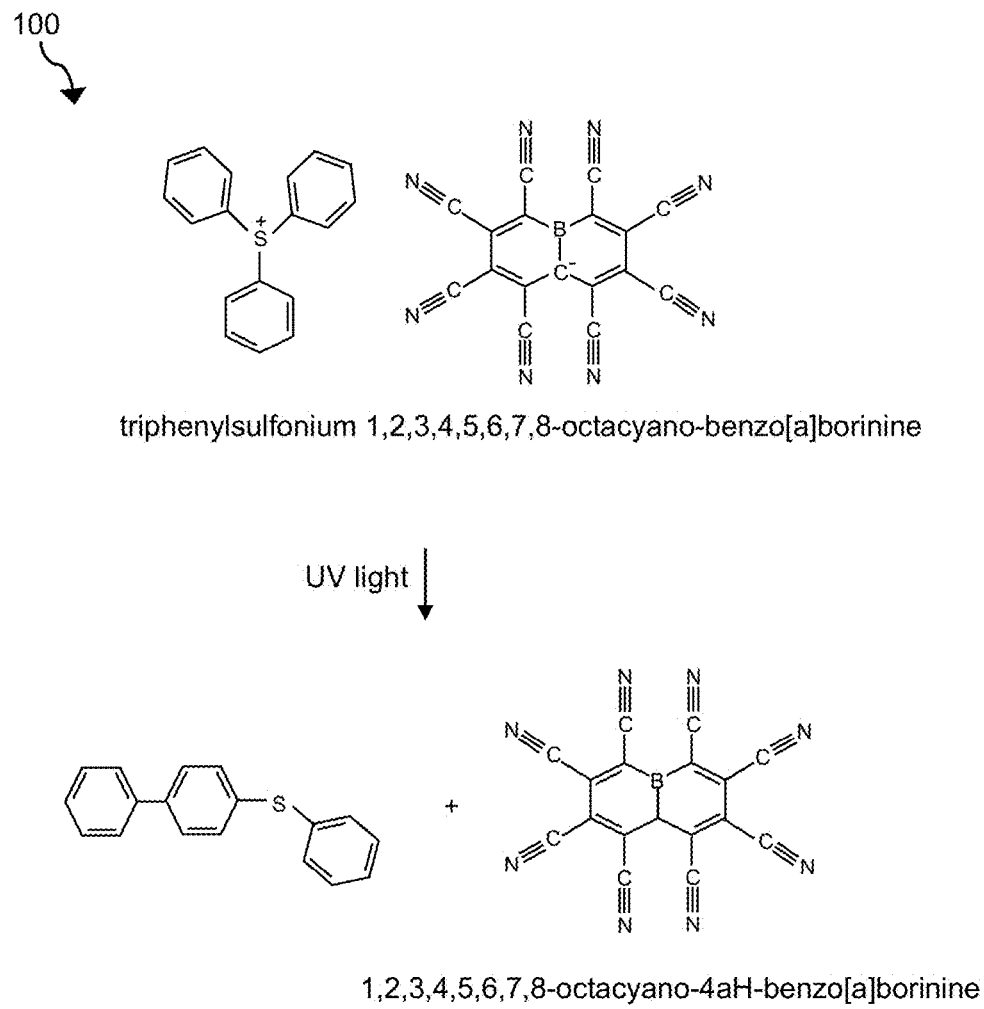
FIG. 1 is a chemical reaction diagram illustrating decomposition of a photoacid generator (PAG) with a fluorine-free anion, according to some embodiments of the present disclosure.

While the disclosure is amenable to various modifications and alternative forms, specifics thereof have been shown by way of example in the drawings, and will be described in detail. It should be understood, however, that the intention is not to limit the disclosure to the particular embodiments described. Instead, the intention is to cover all modifications, equivalents, and alternatives falling within the spirit and scope of the disclosure.

DETAILED DESCRIPTION

Embodiments of the present disclosure are directed to a conjugate base of a superacid and, more specifically, to a photoacid generator anion for a photoacid generator (PAG) for chemically amplified photoresists for deep ultraviolet (DUV) or extreme ultraviolet (EUV) lithography. Further embodiments are directed to methods of forming patterned features on a substrate using the disclosed PAG. While the present disclosure is not necessarily limited to such applications, various aspects of the disclosure may be appreciated through a discussion of examples using this context.

Various embodiments of the present disclosure are described herein with reference to the related drawings, where like numbers refer to the same component. Alternative embodiments can be devised without departing from the scope of the present disclosure. It is noted that various connections and positional relationships (e.g., over, below, adjacent, etc.) are set forth between elements in the following description and in the drawings. These connections and/or positional relationships, unless specified otherwise, can be direct or indirect, and the present disclosure is not intended to be limiting in this respect. Accordingly, a coupling of entities can refer to either a direct or an indirect coupling, and a positional relationship between entities can be a direct or indirect positional relationship.

The following definitions and abbreviations are to be used for the interpretation of the claims and the specification. As used herein, the terms "includes," "comprising," "includes," "including," "has," "having," "contains" or "containing," or any other variation thereof, are intended to cover a non-exclusive inclusion. For example, a composition, a mixture, process, method, article, or apparatus that includes a list of elements is not necessarily limited to only those elements but can include other elements not expressly listed or inherent to such composition, mixture, process, method, article, or apparatus. Further, the word "providing" as used herein can refer to various actions such as creating, purchasing, obtaining, synthesizing, making available, etc. or combinations thereof.

As used herein, the articles "a" and "an" preceding an element or component are intended to be nonrestrictive regarding the number of instances/occurrences of the element or component. Therefore, "a" or "an" should be read to include one or at least one, and the singular word form of the element or component also includes the plural unless the number is obviously meant to be singular.

As used herein, the terms "disclosure" or "present disclosure" are non-limiting terms and not intended to refer to any single aspect of the particular disclosure but encompass all possible aspects as described in the specification and the claims.

Unless otherwise noted, chemical reactions are performed at ambient conditions or under slight heating with no special atmosphere or head space, and may be performed using standard organic solvents to manage mix properties such as viscosity and flow index. Standard procedures for quenching reactions, solvent removal, and purification are performed. Room temperature is between about 15° C. and 30° C. unless otherwise indicated.

Ranges (e.g., time, concentration, temperature, etc.) indicated herein include both endpoints and all numbers between the endpoints. Unless specified otherwise, the use of a tilde (~) or terms such as "about," "substantially," "approximately," "slightly less than," and variations thereof are intended to include the degree of error associated with measurement of the particular quantity based upon the equipment available at the time of filing the application. For example, "about" can include a range of ±8% or 5%, or 2% of a given value, range of values, or endpoints of one or more ranges of values. Unless otherwise indicated, the use of terms such as these in connection with a range applies to both ends of the range (e.g., "approximately 1 g-5 g" should be interpreted as "approximately 1 g-approximately 5 g") and, in connection with a list of ranges, applies to each range in the list (e.g., "about 1 g-5 g, 5 g-10 g, etc." should be interpreted as "about 1 g-about 5 g, about 5 g-about 10 g, etc.").

In carrying out techniques disclosed herein, conventional materials and processing techniques may be employed. For example, the selection of suitable solvents, photosensitizers, pigments, fillers, antistatic agents, flame retardants, defoaming agents, light stabilizers, and antioxidants may be conducted in a conventional manner.

As used herein, the term "aliphatic" encompasses the terms alkyl, alkenyl, and alkynyl, each of which being optionally substituted as set forth below.

As used herein, an "alkyl" group refers to a saturated aliphatic hydrocarbon group containing from 1 to 20 (e.g., 2 to 18, 2 to 8, 2 to 6, or 2 to 4) carbon atoms. An alkyl group can be straight, branched, cyclic, or any combination thereof. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted with one or more substituents or can be multicyclic as set forth below. Unless specified otherwise, the term "alkyl," as well as derivative terms such as "alkoxy" and "thioalkyl," as used herein, include within their scope, straight chain, branched chain, and cyclic moieties.

As used herein, an "alkenyl" group refers to an aliphatic carbon group that contains from 2 to 20 (e.g., 2 to 18, 2 to 8, 2 to 6, or 2 to 4) carbon atoms and at least one double bond. Like an alkyl group, an alkenyl group can be straight, branched, or cyclic, or any combination thereof. Examples of an alkenyl group include, but are not limited to, allyl, isopropenyl, 2-butenyl, and 2-hexenyl. An alkenyl group can be substituted with one or more substituents as set forth below.

As used herein, an "alkynyl" group refers to an aliphatic carbon group that contains from 2 to 20 (e.g., 2 to 18, 2 to 8, 2 to 6, or 2 to 4) carbon atoms and has at least one triple bond. Like an alkyl group, an alkynyl group can be straight, branched, or cyclic, or any combination thereof. Examples of an alkynyl group include, but are not limited to, propargyl and butynyl. An alkynyl group can be substituted with one or more substituents as set forth below.

As used herein, the term "alicyclic" refers to an aliphatic ring compound or group with at least three carbon atoms and the bonds between pairs of adjacent atoms may all be of the type designated single bonds (involving two electrons), or some of them may be double or triple bonds (with four or six electrons, respectively).

A "halogen" is an atom of the group 16 of the periodic table of elements, which includes fluorine, chlorine, bromine, and iodine.

As used herein, an "aryl" group refers to an aromatic ring compound or group having 3 to 30 carbon atoms and used alone or as part of a larger moiety as in "aralkyl," "aralkoxy," or "aryloxyalkyl" and refers to monocyclic (e.g., phenyl); bicyclic (e.g., indenyl, naphthalenyl, tetrahydronaphthyl, or tetrahydroindenyl), and tricyclic (e.g., fluorenyl, tetrahydrofluorenyl, tetrahydroanthracenyl, or anthracenyl) ring systems in which the monocyclic ring system is aromatic or at least one of the rings in a bicyclic or tricyclic ring system is aromatic. The bicyclic and tricyclic groups include benzofused 2- to 3-membered carbocyclic rings. For example, a benzofused group includes phenyl fused with two or more $C_4$ to $C_8$ carbocyclic moieties. An aryl is optionally substituted with one or more substituents as set forth below.

As used herein, an "aralkyl" or "arylalkyl" group refers to an alkyl group (e.g., a $C_1$ to $C_4$ alkyl group) that is substituted with an aryl group. Both "alkyl" and "aryl" have been defined above. An example of an aralkyl group is benzyl. An aralkyl is optionally substituted with one or more substituents as set forth below.

As used herein, a "cycloalkyl" group refers to a saturated carbocyclic mono- to pentacyclic (fused or bridged) ring of 3 to 30 (e.g., 5 to 30) carbon atoms. Examples of cycloalkyl groups can include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2]decyl, bicyclo[2.2.2]octyl, adamantyl, azacycloalkyl, ((aminocarbonyl)cycloalkyl) cycloalkyl, etc.

As used herein, the term "heteroaryl" group refers to a monocyclic, bicyclic, or tricyclic ring system having 3 to 30 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, isoquinolinyl, etc.). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, 1,8-naphthyridyl, etc.

Monocyclic heteroaryls can include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, 1,3,5-triazyl, etc. Monocyclic heteroaryls are numbered according to standard chemical nomenclature.

Bicyclic heteroaryls can include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, pteridyl, etc. Bicyclic heteroaryls are numbered according to standard chemical nomenclature.

The heteroaryl is optionally substituted with one or more substituents as is set forth below.

A "heteroarylalkyl" group, as used herein, refers to an alkyl group (e.g., a $C_1$ to $C_4$ alkyl group) that is substituted with a heteroaryl group. Both "alkyl" and "heteroaryl" have been defined above. A heteroarylalkyl is optionally substituted with one or more substituents as is set forth below.

As used herein, an "acyl" group can refer to a formyl group or an alkylcarbonyl group ($R^X$—C(O)—, where R is an alkyl group).

As used herein, the term "acyloxy" can refer to straight-chain acyloxy, branched-chain acyloxy, cycloacyloxy, cyclic acyloxy, heteroatom-unsubstituted acyloxy, heteroatom-substituted acyloxy, heteroatom-unsubstituted $C_n$-acyloxy, heteroatom-substituted $C_n$-acyloxy, alkylcarbonyloxy, arylcarbonyloxy, alkoxycarbonyloxy, aryloxycarbonyloxy, and carboxylate groups.

As used herein, an "alkoxy" group refers to an alkyl-O— group, where "alkyl" has been defined previously.

As used herein, a "carboxy" group refers to —COOH, —COOR$^X$, —OC(O)H, —OC(O)R$^X$ when used as a terminal group; or —OC(O)— or —C(O)O— when used as an internal group.

As used herein, "alkoxycarbonyl" refers to —COOR, where R is alkyl as defined above, e.g., methoxycarbonyl, ethoxycarbonyl, and the like.

As used herein, a "sulfonate" group refers to R—S(O)$_2$—O$^-$ when used terminally. Sulfonates are the conjugate bases of sulfonic acids with the general formula R—S(O)$_2$—OH. As used herein, a "sulfonic acid" group refers to R—S(O)$_2$—OH when used terminally. As used herein, a "sulfinyl" group refers to —S(O)—R$^X$ when used terminally or —S(O)— when used internally. As used herein, a "sulfonyl" group refers to —S(O)$_2$—R$^X$ when used terminally or —S(O)$_2$— when used internally.

The term "alkylthio" includes straight-chain alkylthio, branched-chain alkylthio, cycloalkylthio, cyclic alkylthio, heteroatom-unsubstituted alkylthio, heteroatom-substituted alkylthio, heteroatom-unsubstituted $C_n$-alkylthio, and heteroatom-substituted $C_n$-alkylthio. In some embodiments, lower alkylthios are contemplated.

As used herein, the term "amine" or "amino" can refer to compounds where a nitrogen atom is covalently bonded to at least one carbon or heteroatom. The term "amine" or "amino" can also refer to —NH$_2$ and substituted moieties. The term "alkyl amino" can refer to species wherein the nitrogen atom is bound to at least one additional alkyl group. The term "dialkyl amino" can refer to species wherein the nitrogen atom is bound to at least two additional independently selected alkyl groups. The term includes "arylamino" and "diarylamino" groups wherein the nitrogen is bound to at least one or two independently selected aryl groups, respectively.

The term "haloalkyl" refers to alkyl groups substituted with from one up to the maximum possible number of halogen atoms. The terms "haloalkoxy" and "halothioalkyl" refer to alkoxy and thioalkyl groups substituted with from one up to five halogen atoms.

The phrase "optionally substituted" is used interchangeably with the phrase "substituted or unsubstituted." As described herein, compounds of the present disclosure can optionally be substituted with one or more substituents, such as are illustrated generally above, or as exemplified by particular classes, subclasses, and species of the present disclosure. As described herein, any of the above moieties or those introduced below can be optionally substituted with one or more substituents described herein. Each substituent of a specific group is further optionally substituted with one to three of halogen, cyano, sulfonyl, sulfinyl, carbonyl, oxoalkoxy, hydroxy, amino, nitro, aryl, haloalkyl, and alkyl. For instance, an alkyl group can be substituted with alkyl sulfonyl and the alkyl sulfonyl can be optionally substituted with one to three of halogen, cyano, sulfonyl, sulfinyl, carbonyl, oxoalkoxy, hydroxy, amino, nitro, aryl, haloalkyl, and alkyl.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a hetero cycloalkyl, can be bound to another ring, such as a cycloalkyl, to form a spiro-bicyclic ring system, e.g., both rings share one common atom. As one of ordinary skill in the art will recognize, combinations of substituents envisioned by this present disclosure are those combinations that result in the formation of stable or chemically feasible compounds.

Modifications or derivatives of the disclosed compounds are contemplated as being useful with the methods and compositions of the present disclosure. Derivatives may be prepared and the properties of such derivatives may be assayed for their desired properties by any method known to those of skill in the art. In certain aspects, "derivative" refers to a chemically modified compound that still retains the desired effects of the compound prior to the chemical modification.

Turning now to an overview of technologies that are more specifically relevant to aspects of the present disclosure, in general, deep ultraviolet (DUV) and extreme ultraviolet (EUV) lithography can be used for semiconductor manufacturing of next generation devices. Photolithography can, using controlled light, define a pattern in a thin photosensitive polymer layer (photoresist) such that the resulting polymer pattern can be transferred into or onto an underlying substrate by etching, deposition, or implantation. Different wavelengths of light can be used. For example, DUV lithography can use 193 nm or 248 nm light, corresponding to an energy of about 6 eV or 5 eV, respectively. EUV lithography can use about 13.5 nm light, which corresponds to an energy of about 92 eV. More specifically, the present disclosure relates to a photoacid generator (PAG) for chemically amplified photoresists for deep ultraviolet (DUV) or extreme ultraviolet (EUV) lithography to be formulated into photoresist compositions.

Photoresists are photosensitive films for transfer of patterns to a substrate. They form negative or positive patterns. After coating a photoresist on a substrate, a source of activating energy, such as ultraviolet light, is used to project a patterned mask or reticle (e.g., using a stepper and a 4× reduction lens assembly) onto the coating to form a latent pattern in the photoresist coating. The mask defines the pattern desired to be transferred to the underlying substrate.

Today, photoresists for DUV and EUV lithography of the 7-nm and 5-nm technology nodes are typically polymer-based chemically amplified photoresists. These photoresist platforms can use photoacid generators (PAGs) and acid-labile polymers. The PAG decomposes upon UV exposure, resulting in an acid and degradation products. Examples of PAGs can include sulfonium salts with fluorinated anions, such as triphenylsulfonium tris(trifluoromethylsulfonyl)methide. Upon UV exposure, the carbon-sulfur bond in these sulfonium salts undergoes radical cleavage, generating a fluorinated acid. An acid-labile polymer is a polymer (e.g., a fluorine-free polymer) with an acid-labile protecting group. Removal of the protecting group by an acid can form alkali-soluble or volatile compounds.

However, the toxicity of fluorinated materials has been the focus of increasing concern and scrutiny. For example, the European Union (EU) is implementing regulatory actions to control and phase down fluorinated materials such as perfluorocarbons and sulfur hexafluoride. Therefore, alternatives to fluorinated anions for chemically-amplified photoresists are necessary. Examples, of existing fluorine-free PAGs include p-toluenesulfonate anions and camphor-sulfonic anions. However, these anions have relatively low acid-dissociation constants (e.g., about 18 orders of magnitude smaller than that of tris(trifluoromethylsulfonyl)methane), which limits their usefulness in chemically amplified photoresists for DUV and EUV lithography.

Another key metric of photoresists is sensitivity, which refers to the UV energy required to print a feature in the photoresist. Available chemically amplified photoresists for EUV lithography commonly have lower than optimal sensitivities.

Disclosed herein is a conjugate base of a superacid that can be a photoacid generator (PAG) anion to be formulated into chemically amplified photoresist compositions. These photoresists can be used in lithographic processes, such as when DUV or EUV radiation is used. In some embodiments, PAGs that include the disclosed conjugated bases/anions can be fluorine-free PAGs and may overcome disadvantages of existing photoresist materials, such as toxicity, chemical waste production, low acid-dissociation constant, and low sensitivity. Additionally, the disclosed PAGs can be used in semiconductor fabrication without changes to an existing process flow.

The disclosed PAG anions can be conjugate bases of superacids. The Brønsted-Lowry acid-base theory includes the concepts of conjugate acids (AH) and conjugate bases (A$^-$). When an acid dissociates into its ions in water, it loses a proton (H$^+$). The species that is formed is the acid's conjugate base. A more general definition is that a conjugate base is the base member of a pair of compounds that transform into each other by gaining or losing a proton. The conjugate base is able to gain a proton. The conjugate acid can donate a proton. The conjugate base may be recognized as an anion.

In some embodiments, the acid-dissociation constant of the conjugate acid (e.g., a superacid) of the PAG anion generated upon UV exposure can be tuned by influencing the delocalization of the negative elementary charge on the C atom by the choice of the electron acceptor atom and/or by the choice of the electron-withdrawing group substituents. This tuning can affect the stabilization of the negative elementary charge by influencing the delocalization of the negative elementary charge.

The PAG anions can include an alkyl group, a monocyclic aromatic hydrocarbon group ("monocyclic group"), or a bicyclic aromatic hydrocarbon group ("bicyclic group") in some embodiments. The alkyl group of the PAG anion can be a saturated aliphatic hydrocarbon group containing from 1 to 10 (e.g., 2 to 8, 2 to 8, 2 to 6, or 2 to 4) carbon atoms. The alkyl group can be straight, branched, cyclic, or any combination thereof. Examples of alkyl groups include, but are not limited to, methyl, ethyl, propyl, isopropyl, butyl, isobutyl, sec-butyl, tert-butyl, n-pentyl, n-hexyl, n-heptyl, or 2-ethylhexyl, n-octyl, n-nonyl, or n-decyl. The alkyl group may be substituted with one or more substituents.

Monocyclic aromatic hydrocarbon groups are composed of a single aromatic ring, for example benzene, toluene, ethylbenzene, and xylenes. Bicyclic aromatic hydrocarbon groups can contain two benzene rings, such as naphthalene. The aromatic hydrocarbons groups can possess one or more aromatic rings in their structures. Aromatic hydrocarbons are unsaturated hydrocarbons with sigma bonds, and the □-electrons are delocalized between carbon atoms forming a circle. In contrast, aliphatic hydrocarbons lack this delocalization. The aromatic ring according to the present disclosure can be a four-, five-, six-, or seven-membered ring. In some embodiments, the aromatic hydrocarbons have the general chemical formula $C_nH_n$. In some embodiments, the aromatic hydrocarbon group contains a benzene ring. The benzene ring is stabilized by resonance, and the □-electrons in the ring structure are delocalized.

Each PAG anion can also include an electron acceptor atom. The electron acceptor atom of the PAG anion can be boron(III), aluminum(III), or phosphorus(V) in some embodiments. The electron acceptor atom can be covalently bonded to a carbon atom (C) of the alkyl group or the monocyclic or bicyclic hydrocarbon group that has a negative elementary charge.

The alkyl group or the monocyclic or bicyclic aromatic hydrocarbon group has at least one electron-withdrawing group. An electron-withdrawing group or substituent refers to a moiety that draws electrons away from a reaction center or the atom to which it is bonded. When this center is an electron rich carbanion, the presence of the electron-withdrawing substituent has a stabilizing effect. Examples of electron-withdrawing groups can be, for example, halogens (e.g., F or Cl), nitriles (CN), sulfonyls $(RS(O)_2R^1)$, sulfinyls $(RS(O)R^1)$, carbonyls $(RC(O)R^1)$, nitro groups $(NO_2)$, etc.

The number of electron-withdrawing groups can depend on the number of valences of the PAG anion (e.g., whether the PAG anion has an alkyl group or a monocyclic or bicyclic aromatic hydrocarbon group). If the PAG anion includes an alkyl group (e.g., a methyl group), the number of electron-withdrawing group(s) can be one, two, three, or four. If the PAG anion includes a six-membered monocyclic aromatic hydrocarbon group, the number of electron-withdrawing group(s) can be one, two, three, four, five, or six. If the PAG anion includes a six-membered bicyclic aromatic hydrocarbon group, the number of electron-withdrawing group(s) can be one, two, three, four, five, six, seven, eight, nine, or ten.

In some embodiments, the disclosed PAG anions can be represented by the general formula (I):

(I)

wherein X represents an electron acceptor atom (boron(III), aluminum(III), or phosphorus(V)) covalently bound to a carbon atom (C) with a negative elementary charge. At least one of group(s) R1, R2, R3 and/or R4, independently from one another, include(s) at least one electron-withdrawing substituent. These are referred to herein as "electron-withdrawing R groups". Any remaining group(s) R1, R2, R3 and/or R4 can be, independently from one another, non-electron-withdrawing groups. Examples of electron-withdrawing and non-electron-withdrawing groups that may be used are discussed in greater detail below.

The PAG anion of general formula (I) includes an alkyl group. The alkyl group can be a methyl group, as is illustrated herein. However, any appropriate alkyl group can be used (e.g., a saturated aliphatic hydrocarbon group containing from 1 to 10 (e.g., 2 to 8, 2 to 8, 2 to 6, or 2 to 4) carbon atoms). The alkyl group can be straight, branched, cyclic, or any combination thereof. Examples of alkyl groups include methyl, ethyl, propyl, isopropyl, butyl, isobutyl, sec-butyl, tert-butyl, n-pentyl, n-hexyl, n-heptyl, or 2-ethylhexyl, n-octyl, n-nonyl, or n-decyl, etc. The alkyl group can optionally be substituted with one or more substituents.

In further embodiments, the PAG anions can be represented by the general formula (II):

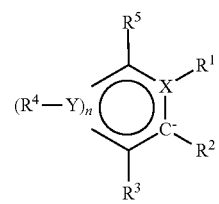

(II)

wherein X represents an electron acceptor atom (boron(III) or aluminum(III)) covalently bound to a carbon atom (C) with a negative elementary charge. Y represents a methylene group, and n is 0 or an integer in a range from 1 to 3. At least one of R1, R2, R3, R4, and R5 include(s), independently from one another, at least one electron-withdrawing substituent. These are referred to herein as "electron-withdrawing R groups". Any remaining group(s) R1, R2, R3, R4, and/or R5 can be, independently from one another, non-electron-withdrawing R group(s).

The PAG anion of the general formula (II) includes a monocyclic aromatic hydrocarbon group ("monocyclic group"). The size of the monocyclic group is indicated by "n", which can either be 0 or an integer in a range from 1 to 3. If n=0, the monocyclic aromatic hydrocarbon group is a four membered aromatic ring. If f n=1, the monocyclic aromatic hydrocarbon group is a five membered aromatic ring. If n=2, the monocyclic aromatic hydrocarbon group is a six membered aromatic ring. If n=3, the monocyclic aromatic hydrocarbon group is a seven membered aromatic ring. In some embodiments, the PAG anion of the general formula (II) includes a six membered aromatic ring.

The maximum number of electron-withdrawing R groups depends on the number of "n" in the general formula (II). In some embodiments, the PAG anion of the general formula (II) has up to n plus four electron-withdrawing R groups (e.g., one, two, three, four, five, six, or seven electron-withdrawing groups).

In some embodiments, in formula (II) at least two adjacent groups R1, R2, R3, R4 or R5 are linked with each other via a C atom of an alkyl group by a covalent bond. In some embodiments, in formula (II) the adjacent groups R1 and R5 and/or the adjacent groups R2 and R3 are linked with each other as described above. If the at least two adjacent groups are linked with each other, an additional aromatic ring is obtained, defined by the linkage of the two adjacent groups with each other. The size of the generated aromatic ring depends on the linkage site or binding site between the two adjacent R groups and in particular the number of C-atoms of the alkyl groups.

In some embodiments, by the linkage of the two adjacent groups, a five-, six-, or seven-membered aromatic ring, and thus a multicycle ring, is obtained. A five-membered aromatic ring or a seven-membered aromatic ring may be obtained by the linkage of the two adjacent groups R1 and R5 or R2 and R3 of formula (II). Two five-membered aromatic rings or two seven-membered aromatic rings may be obtained by the linkage of the two adjacent groups R1 and R5 and the adjacent groups R2 and R3 of formula (II). By such linkage, the anion's negative charge delocalization can be enhanced. In order to further influence the delocalization of the negative elementary charge, the generated five-, six-, or seven-membered aromatic ring can include at least one electron-withdrawing group. In some embodiments, all C-atoms in the ring have an electron-withdrawing group.

In additional embodiments, the PAG anions can be represented by the general formula (III):

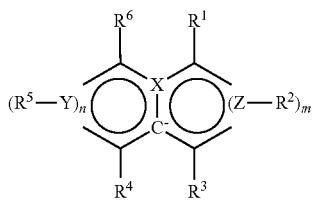

(III)

wherein X represents an electron acceptor atom (boron(III) or aluminum(III)) covalently bound to a carbon atom (C) with a negative elementary charge. Y and Z represent methylene groups, and n and m represent, independently from each other, 0 or integers in a range from 1 to 3. At least one of group(s) R1, R2, R3, R4, R5, and R6 include(s), independently from one another, electron-withdrawing substituents(s). These are referred to herein as "electron-withdrawing R groups". Any remaining R group(s) can be, independently from one another, non-electron-withdrawing R group(s).

The PAG anion of the general formula (III) has a bicyclic condensed aromatic hydrocarbon group ("bicyclic aromatic group"). The bicyclic aromatic group includes two four-, five-, six-, or seven-membered aromatic rings. The two rings can either be the same or different. That is, the bicyclic aromatic group can be a combination of a four-membered ring with a four-, five-, six-, or seven-membered ring, a combination of a five-membered ring with a five-, six-, or seven-membered ring, a combination of a six-membered ring with a six- or seven-membered ring, or a combination of a seven-membered ring with a seven-membered ring. In some embodiments, the bicyclic aromatic group is naphthalene.

The numbers "n" and "m" define the sizes of monocyclic aromatic hydrocarbon groups in the general formula (III). "n" and "m" can either be 0 or can be an integer in a range from 1 to 3. If n=0 and m=0, the bicyclic aromatic hydrocarbon group has two four membered aromatic rings; if n=1 and m=1, the bicyclic aromatic hydrocarbon group has two five membered aromatic rings; if n=2 and m=2, the bicyclic aromatic hydrocarbon group has two six membered aromatic rings; and if n=3 and m=3, the bicyclic aromatic hydrocarbon group has two seven membered aromatic rings. In some embodiments, the PAG anion of the general formula (III) includes two six membered aromatic rings.

The maximum number of electron-withdrawing groups depends on the number of "n" and "m" in the general formula (III). In some embodiments, the PAG anion of the general formula (III) includes up to n plus m plus four electron-withdrawing groups (e.g., one, two, three, four, five, six, seven, eight, nine, or ten electron-withdrawing group substituents).

For the PAG anion's negative charge delocalization, the electron acceptor atom X can be covalently bonded to a carbon atom (C) on the interface between the two condensed aromatic hydrocarbon groups/aromatic rings/cycles.

In formula (III), at least two adjacent R groups may be linked with each other via a covalent bond between alkyl carbons. For example, the adjacent groups R1 and R6 and/or the adjacent groups R3 and R4 of formula (III) can be linked with each other as described above. If the adjacent groups are linked with each other, an additional aromatic ring is obtained. The size of the generated aromatic ring depends on the linkage site or binding site between the two adjacent R groups and in particular the number of C-atoms of the alkyl groups. In some embodiments, by the linkage of the two adjacent groups a multicycle ring is obtained (e.g., a five-, six-, or seven-membered aromatic ring). In some embodiments, a five-membered aromatic ring or a seven-membered aromatic ring is obtained by the linkage of the two adjacent groups R1 and R6 or the adjacent groups R3 and R4 of formula (III). In further embodiments, two five-membered aromatic rings or two seven-membered aromatic rings are obtained by the linkage of the two adjacent groups R1 and R6 and the adjacent groups R3 and R4 of formula (III). By such linkage, the anion's negative charge delocalization can be enhanced. In order to further influence the delocalization of the negative elementary charge the generated five, six or seven membered aromatic ring includes at least one electron-withdrawing group. In some embodiments, all C atoms in the thus generated ring have an electron-withdrawing group.

Examples of electron-withdrawing groups in the general formulas (I), (II), and (III) can include cyano, linear or branched $C_1$ to $C_4$ cyanoalkyl, linear or branched $C_1$ to $C_4$ cyanoalkenyl, $C_1$ to $C_4$ alkylsulfonyl, linear or branched $C_1$ to $C_4$ ($C_1$ to $C_4$ alkylsulfonyl)alkyl, linear or branched $C_1$ to $C_4$ ($C_1$ to $C_4$ alkylsulfonyl)alkenyl, or derivatives thereof. In some embodiments, electron-withdrawing R groups can include cyano, cyanoimino, linear or branched $C_1$ to $C_4$ cyanoalkyl, linear or branched $C_1$ to $C_4$ cyanoalkenyl, linear or branched $C_1$ to $C_4$ cyanoalkylene, $C_1$ to $C_4$ alkylsulfonyl, ($C_1$ to $C_4$ alkylsulfonyl)imino, linear or branched $C_1$ to $C_4$ ($C_1$ to $C_4$ alkylsulfonyl)alkyl, linear or branched $C_1$ to $C_4$ ($C_1$ to $C_4$ alkylsulfonyl)alkenyl, linear or branched $C_1$ to $C_4$ ($C_1$ to $C_4$ alkylsulfonyl)alkylene, or derivatives thereof. In some embodiments, examples of electron-withdrawing groups include cyanoethenyl, dicyanoethenyl, tricyanoethenyl, methylsulfonyl, methylsulfonylimino, cyanomethylene, dicyanomethylene, methylsulfonylmethylene, and bis(methylsulfonyl)methylene.

In, for example, applications in which toxicity and chemical waste are of less concern, electron-withdrawing R groups in general formulas (I), (II), and (III) may include fluoro, fluoroimino, linear or branched $C_1$ to $C_8$ fluoroalkyl, linear or branched $C_1$ to $C_8$ fluoroalkylimino, linear or branched $C_1$ to $C_8$ fluoroalkenyl, linear or branched $C_1$ to $C_8$ fluoroalkylene, ($C_1$ to $C_4$ fluoroalkyl)sulfonyl, ($C_1$ to $C_4$ fluoroalkyl) sulfonylimino, linear or branched $C_1$ to $C_4$ ($C_1$ to $C_4$ fluoroalkyl)sulfonylalkyl, linear or branched $C_1$ to $C_4$ ($C_1$ to $C_4$ fluoroalkyl)sulfonylalkenyl, linear or branched $C_1$ to $C_4$ ($C_1$ to $C_4$ fluoroalkyl)sulfonylalkylene, $C_3$ to $C_7$ fluorocycloalkyl, ($C_3$ to $C_7$ fluorocycloalkyl)imino, $C_5$ to $C_7$ fluoroaryl, ($C_5$ to $C_7$ fluoroaryl)imino, and derivatives thereof. In some embodiments, these electron-withdrawing R groups can include trifluoromethyl, pentafluoroethyl, heptafluoropropyl, trifluoromethylsulfonyl, fluoroimino, trifluoromethylimino, trifluoromethylsulfonylimino, bis(trifluoromethyl)methylene, and bis(trifluoromethylsulfonyl)methylene. Additional examples may include difluoromethyl, fluoroethyl, difluoroethyl, trifluoroethyl, tetrafluoroethyl, fluoropropyl, difluoropropyl, trifluoropropyl, tetrafluoropropyl, pentafluoropropyl, hexaafluoropropyl, trifluoromethylsulfonyl, fluoromethylimino, difluoromethylimino, trifluoromethylmethylene, and trifluoromethylsulfonylmethylene.

Examples of non-electron-withdrawing R groups that may be included in the general formulas (I), (II), and (III) can include a hydrogen atom (H), optionally substituted linear or branched alkyl, optionally substituted cycloalkyl, optionally substituted aryl, optionally substituted saturated or unsaturated heterocyclic group, or a derivative thereof.

If a PAG anion of the general formula (I), (II), or (III) has more than one electron-withdrawing R group, the electron-withdrawing R groups can be the same or different. If a PAG anion has more than one non-electron-withdrawing R group, the non-electron-withdrawing R groups can be the same or different.

Herein, the term "at least one electron-withdrawing substituent" indicates that a given R group in the general formulas (I), (II), and (III) includes one or more electron-withdrawing substituents(s), depending on the nature and valency of the electron-withdrawing group. For example, if the electron-withdrawing R group is a fluoromethyl group, the methyl group can have one, two or three electron-withdrawing fluoro substituents. If the electron-withdrawing R group is a cyanoethylene group, the ethylene group can have one, two or three electron-withdrawing cyano substituents.

Further, the term "remaining group(s) R1, R2, R3, R4, R5, and/or R6" or "remaining R groups" refers to groups R1, R2, R3, R4, R5 and/or R6 in the general formulas (I), (II), and (III) which do not include an electronic-withdrawing substituent. For example, if only R1 in the general formula (III) has an electron-withdrawing substituent (e.g., cyano), the remaining groups R2, R3, R4, R5 and R6 are non-electron-withdrawing groups.

In some embodiments, the PAG anion is selected from 2-(dicyanoboranyl)propanedinitrile anion, bis(methylsulfonyl)boranyl-bis(methylsulfonyl)methane anion, dicyanoboranyl-bis(methylsulfonyl)methane anion, 2-(bis(trifluoromethyl)boranyl)-1,1,1,3,3,3-hexafluoropropane anion, bis (trifluoromethylsulfonyl)boranyl-bis (trifluoromethylsulfonyl)methane anion, dicyanoboranyl-bis (trifluoromethylsulfonyl)methane anion, 2-(dicyanoaluminyl)propanedinitrile anion, bis(methylsulfonyl)aluminyl-bis(methylsulfonylmethane anion, dicyanoaluminyl-bis(methylsulfonylmethane anion, 2-(bis(trifluoromethyl)aluminyl)-1,1,1,3,3,3-hexafluoropropane anion, bis(trifluoromethylsulfonyl)aluminyl-bis(trifluoromethylsulfonyl)methane anion, dicyanoaluminyl-bis(trifluoromethylsulfonyl)methane anion, bis(cyanoimino)(dicyanomethyl)phosphorane anion, bis(methylsulfonylimino)-bis (methylsulfonyl)methylphosphorane anion, bis (trifluoromethylimino)(1,1,1,3,3,3-hexafluoroprop-2-yl) phosphorane anion, bis(trifluoromethylsulfonylimino)-bis (trifluoromethylsulfonyl)methylphosphorane anion, bis (dicyanomethylene)(dicyanomethyl)phosphorane anion, bis (bis(methylsulfonyl)methylene)-bis(methylsulfonyl) methylphosphorane anion, bis(bis(trifluoromethyl) methylene)(1,1,1,3,3,3-hexafluoroprop-2-yl)phosphorane anion, bis(bis(trifluoromethylsulfonyl)methylene)-bis(trifluoromethylsulfonyl)methylphosphorane anion, 1,2,3,4,5,6-hexacyanoborinine anion, 1,2,3,4,5,6-hexakis(methylsulfonyl)borinine anion, 1-cyano-2,3,4,5,6-pentakis (methylsulfonyl)borinine anion, 1,2,3,4,5,6-hexakis (trifluoromethyl)borinine anion, 1,2,3,4,5,6-hexakis (trifluoromethylsulfonyl)borinine anion, 1-cyano-2,3,4,5,6-pentakis(trifluoromethylsulfonyl)borinine anion, 1,2,3,4,5,6-hexacyanoaluminine anion, 1,2,3,4,5,6-hexakis (methylsulfonyl)aluminine anion, 1-cyano-2,3,4,5,6-pentakis(methylsulfonyl)aluminine anion, 1,2,3,4,5,6-hexakis(trifluoromethyl)aluminine anion, 1,2,3,4,5,6-hexakis(trifluoromethylsulfonyl)aluminine anion, 1-cyano-2,3,4,5,6-pentakis(trifluoromethylsulfonyl)aluminine anion, 1,2,3,4,5,6,7,8-octacyanobenzo[a]borinine anion, 1,8-(1,2,3,4-tetracyanobuta[1,3]dieno)-2,3,4,5,6,7-hexacyanobenzo [a]borinine anion, bis-[1,8:4,5]-(1,2,3,4-tetracyanobuta[1,3] dieno)-2,3,6,7-tetracyanobenzo[a]borinine anion, 1,2,3,4,5,6,7,8-octacyanobenzo[a]aluminine anion, 1,8-(1,2,3,4-tetracyanobuta[1,3]dieno)-2,3,4,5,6,7-hexacyanobenzo[a] aluminine anion, bis-[1,8:4,5]-(1,2,3,4-tetracyanobuta[1,3] dieno)-2,3,6,7-tetracyanobenzo[a]aluminine anion, 1,2,3,4,5,6-hexakis(methylsulfonyl)borinine anion, 1-cyano-2,3,4,5,6-pentakis(methylsulfonyl)borinine anion, 1,2,3,4,5,6,7,8-octakis(methylsulfonyl)benzo[a]borinine anion, 1,2,3,4,5,6-hexakis(methylsulfonyl)aluminine anion, 1-cyano-2,3,4,5,6-pentakis(methylsulfonyl)aluminine anion, and 1,2,3,4,5,6,7,8-octakis(methylsulfonyl)benzo[a]aluminine anion.

FIG. 1 is a chemical reaction diagram 100 illustrating a PAG with a fluorine-free anion, according to some embodiments of the present disclosure. The illustrated triphenylsulfonium, 1,2,3,4,5,6,7,8-octacyano-benzo[a]borinine. Upon UV (e.g., EUV or DUV) exposure, the C—S bond in the sulfonium cation undergoes radical cleavage and an acid, 1,2,3,4,5,6,7,8-octacyano-4aH-benzo[a]borinine, is generated.

Figure 2:
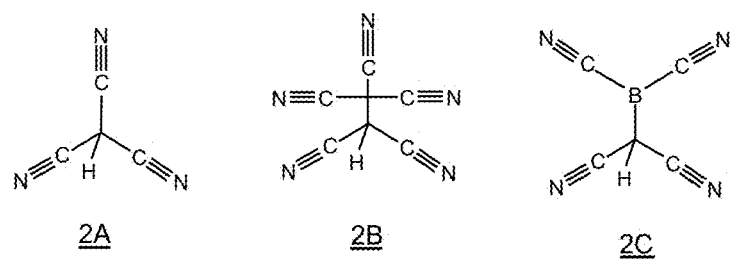
FIG. 2 illustrates chemical structure diagrams of acids with cyano groups, according to some embodiments of the present disclosure.

FIG. 2 illustrates examples of acids 2A, 2B, and 2C with cyano groups, according to some embodiments of the present disclosure. Ab initio gas phase simulation of proton dissociation at the Perdew-Burke-Esnzerof and double-zeta valence polarizations (PBE/DZVP) level of theory were performed on the acids, methanetricarbonitrile 2A, ethane-1,1,1,2,2-pentacarbonitrile 2B (based on alkanes with cyano group substituents), and 2-(dicyanoboranyl)propanedinitrile (based instead on a heteroalkane with cyano group substituents) 2C. The proton dissociation energies determined for the acids 2A-2C are, respectively, 256 kcal/mol, 260 kcal/mol, and 231 kcal/mol. The lower the proton dissociation energy, the more labile the proton, or the "stronger" the acid. The determined proton dissociation energies can be compared to PAG acids well-known in the art, tris(trifluoromethylsulfonyl)methane (255 kcal/mol), as well as p-toluenesulfonic acid and camphorsulfonic acid (both 284 kcal/mol).

It is noted that methanetricarbonitrile 2A has a proton dissociation energy (256 kcal/mol) similar to that of tris(trifluoromethylsulfonyl)methane (255 kcal/mol). That is, the acid-dissociation constant of methanetricarbonitrile 2A can be similar to that of tris(trifluoromethylsulfonyl)methane. Furthermore, it is noted that increasing the number of cyano groups does not necessarily lead to a lower proton dissociation energy. For example, ethane-1,1,1,2,2-pentacarbonitrile 2B, which includes five cyano groups, has a proton dissociation energy (260 kcal/mol) similar to that of methanetricarbonitrile 2A (256 kcal/mol), which has three cyano groups. Additionally, the heteroalkane 2-(dicyanoboranyl)propanedinitrile 2C, which includes B(III) and four cyano groups, has a substantially lower proton dissociation energy (231 kcal/mol) than those of the alkanes ethane-1,1,1,2,2-pentacarbonitrile 2B and methanetricarbonitrile 2A.

A Mulliken population analysis was used to estimate the partial atomic charges of the acids shown in FIG. 2 after proton dissociation. For methanetricarbonitrile 2A after proton dissociation, net charges of −0.27 for the deprotonated C atom and −0.24 for each of its three cyano groups were obtained. The negative elementary charge on methanetricarbonitrile after deprotonation is delocalized over the entire molecule.

For the alkane ethane-1,1,1,2,2-pentacarbonitrile 2B after proton dissociation, net charges of −0.17 for the deprotonated C atom (C at position 2), −0.24 for each of its two attached cyano groups, −0.33 for the further C atom (C at position 1), and −0.01 for each of its three cyano groups were obtained. The negative elementary charge on ethane-1,1,1,2,2-pentacarbonitrile 2B after deprotonation is not delocalized over the entire molecule. The increased number of cyano groups (compared to three cyano groups for methanetricarbonitrile 2A) therefore may not lead to an enhanced stability of the anion or, concomitantly, a lower proton dissociation energy of ethane-1,1,1,2,2-pentacarbonitrile 2B.

For the heteroalkane 2-(dicyanoboranyl)propanedinitrile 2C after proton dissociation, net charges of −0.21 for the deprotonated C atom, −0.16 for each of its two attached cyano groups, −0.18 for the B atom, and about −0.14 for each of its two cyano groups were obtained. The negative elementary charge on 2-(dicyanoboranyl)propanedinitrile 2C after deprotonation is delocalized over the entire molecule. The increased number of cyano groups (compared to three cyano groups for methanetricarbonitrile 2A) may therefore lead to an enhanced stability of the anion and, concomitantly, to a lower proton dissociation energy of 2-(dicyanoboranyl)propanedinitrile 2C.

The ability to stabilize the conjugate acid through the electronic effect may be the microscopic origin of 2-(dicyanoboranyl)propanedinitrile's low proton dissociation energy, which is a measure of the relative stability of the acid and its conjugate. Microscopic mechanisms can include also structural effects such as those shown in FIG. 3.

Figure 3:
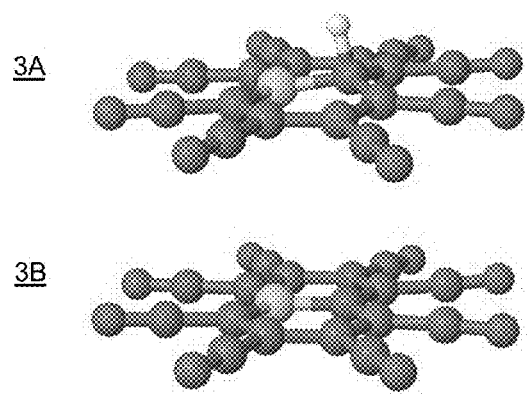
FIG. 3 illustrates molecular structures of a PAG anion and corresponding acid generated upon UV exposure, according to some embodiments of the present disclosure.

FIG. 3 illustrates molecular structures of a PAG anion and corresponding acid generated upon UV exposure, according to some embodiments of the present disclosure. These structures were obtained by ab initio simulation. The acid 3A is heteroaromatic 1,2,3,4,5,6,7,8-octacyano-4aH-benzo[a]borinine, and the PAG anion 3B is 1,2,3,4,5,6,7,8-octacyano-benzo[a]borinine anion. The anion 3B can be formed after proton dissociation of 1,2,3,4,5,6,7,8-octacyano-4aH-benzo[a]borinine 3A.

The C atom at position 4a of the benzo[a]borinine structure 3A, which forms a C—H bond, is in $sp^3$ hybridization and concomitantly in tetrahedral coordination. The tetrahedral coordinated C atom deforms the heteroaromatic bicycle into a non-planar geometry, which raises the molecule's internal energy.

In the PAG anion structure 3B, the cycle atoms are in $sp^2$ hybridization and concomitantly in trigonal coordination. The heteroaromatic bicycle of 3B has a planar geometry. Furthermore, the negative elementary charge of the 1,2,3,4,5,6,7,8-octacyano-benzo[a]borinine anion 3B is delocalized over the C atom at position 4a, the B atom (which is a p-orbital electron acceptor), and the two aromatic rings. The in total ten conjugated electrons are delocalized over the heteroaromatic bicycle, which has π-bonds in resonance that can enhance the anion's stability.

The microscopic origin of the low proton dissociation energy of 1,2,3,4,5,6,7,8-octacyano-4aH-benzo[a]borinine 3A, which is a measure of the relative stability of the acid and its conjugate, can include the ability to stabilize the conjugate acid through the structural modification and electronic effects.

Figure 4:
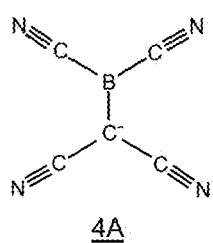
FIG. 4 illustrates chemical structure diagrams of PAG anions, according to some embodiments of the present disclosure.
Figure 4:
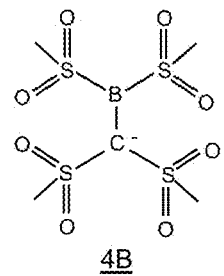
Figure 4:
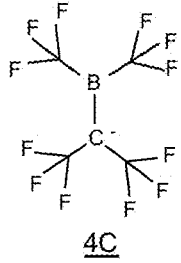
Figure 4:
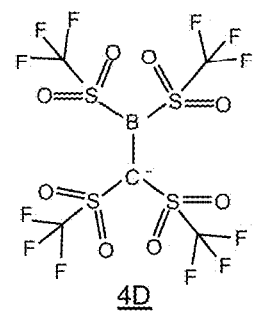
Figure 4:
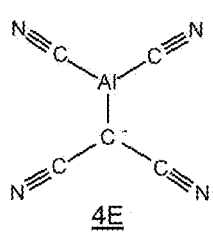
Figure 4:
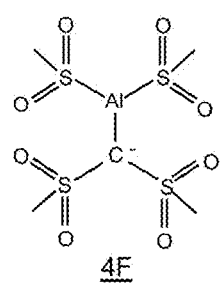
Figure 4:
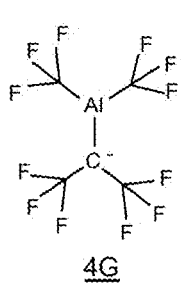
Figure 4:
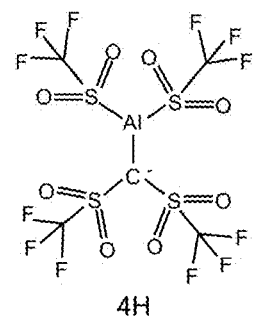
Figure 4:
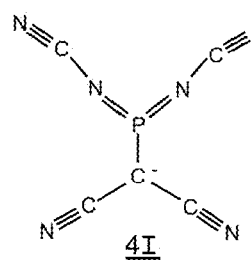
Figure 4:
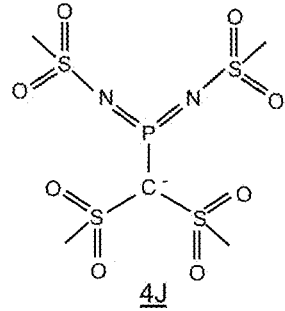
Figure 4:
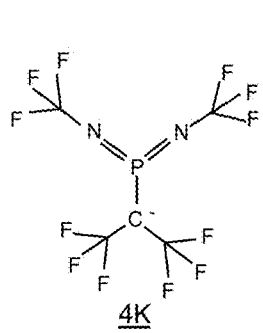
Figure 4:
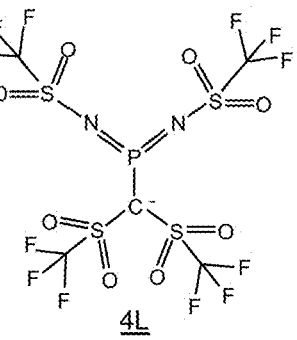
Figure 4:
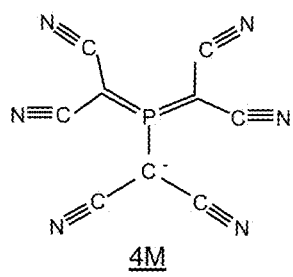
Figure 4:
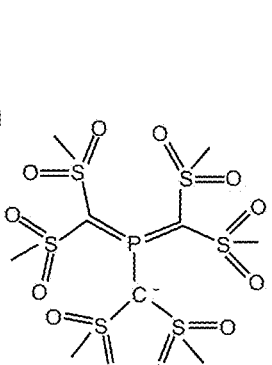
Figure 4:
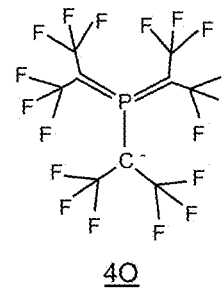
Figure 4:
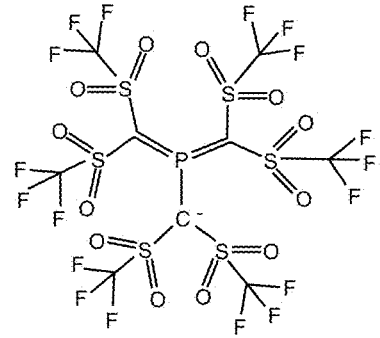

FIG. 4 illustrates examples of PAG anions 4A-4P of general formula (I), according to some embodiments of the present disclosure. Each of the PAG anions 4A-4P includes a heteroalkene methylborane, methylalumane, or methylphosphorane. The electron acceptor atom B(III), Al(III), or P(V) is arranged in such a way that each anion includes a covalent bond between a B(III), Al(III), or P(V) atom and a C atom with a negative elementary charge. Each of the illustrated PAG anions 4A-4P further includes cyano, methylsulfonyl, trifluoromethyl, trifluoromethylsulfonyl, cyanoimino, methylsulfonylimino, trifluoromethylimino, trifluoromethylsulfonylimino, dicyanomethylene, bis(methylsulfonyl)methylene, bis(trifluoromethyl)methylene, or bis(trifluoromethylsulfonyl)methylene electron-withdrawing groups.

The illustrated PAG anions of formula (I) include 2-(dicyanoboranyl)propanedinitrile anion 4A, bis(methylsulfonyl)boranyl-bis(methylsulfonyl)methane anion 4B, 2-(bis(trifluoromethyl)boranyl)-1,1,1,3,3,3-hexafluoropropane anion 4C, bis(trifluoromethylsulfonyl)boranyl-bis(trifluoromethylsulfonyl)methane anion 4D, 2-(dicyanoaluminyl)propanedinitrile anion 4E, bis(methylsulfonyl)aluminyl-bis(methylsulfonyl)methane anion 4F, 2-(bis(trifluoromethyl)aluminyl)-1,1,1,3,3,3-hexafluoropropane anion 4G, bis(trifluoromethylsulfonyl)aluminyl-bis(trifluoromethylsulfonyl)methane anion 4H, bis(cyanoimino)(dicyanomethyl)phosphorane anion 4I, bis(methylsulfonylimino)-bis(methylsulfonyl)methylphosphorane anion 4J, bis(trifluoromethylimino)(1,1,1,3,3,3-hexafluoroprop-2-yl)phosphorane anion 4K, bis(trifluoromethylsulfonylimino)-bis(trifluoromethylsulfonyl)methylphosphorane anion 4L, bis(dicyanomethylene)(dicyanomethyl)phosphorane anion 4M, bis(bis(methylsulfonyl)methylene)-bis(methylsulfonyl)

methylphosphorane anion 4N, bis(bis(trifluoromethyl)methylene)(1,1,1,3,3,3-hexafluoroprop-2-yl)phosphorane anion 4O, and bis(bis(trifluoromethylsulfonyl)methylene)-bis(trifluoromethylsulfonyl)methyl-phosphorane anion 4P.

Figure 5:
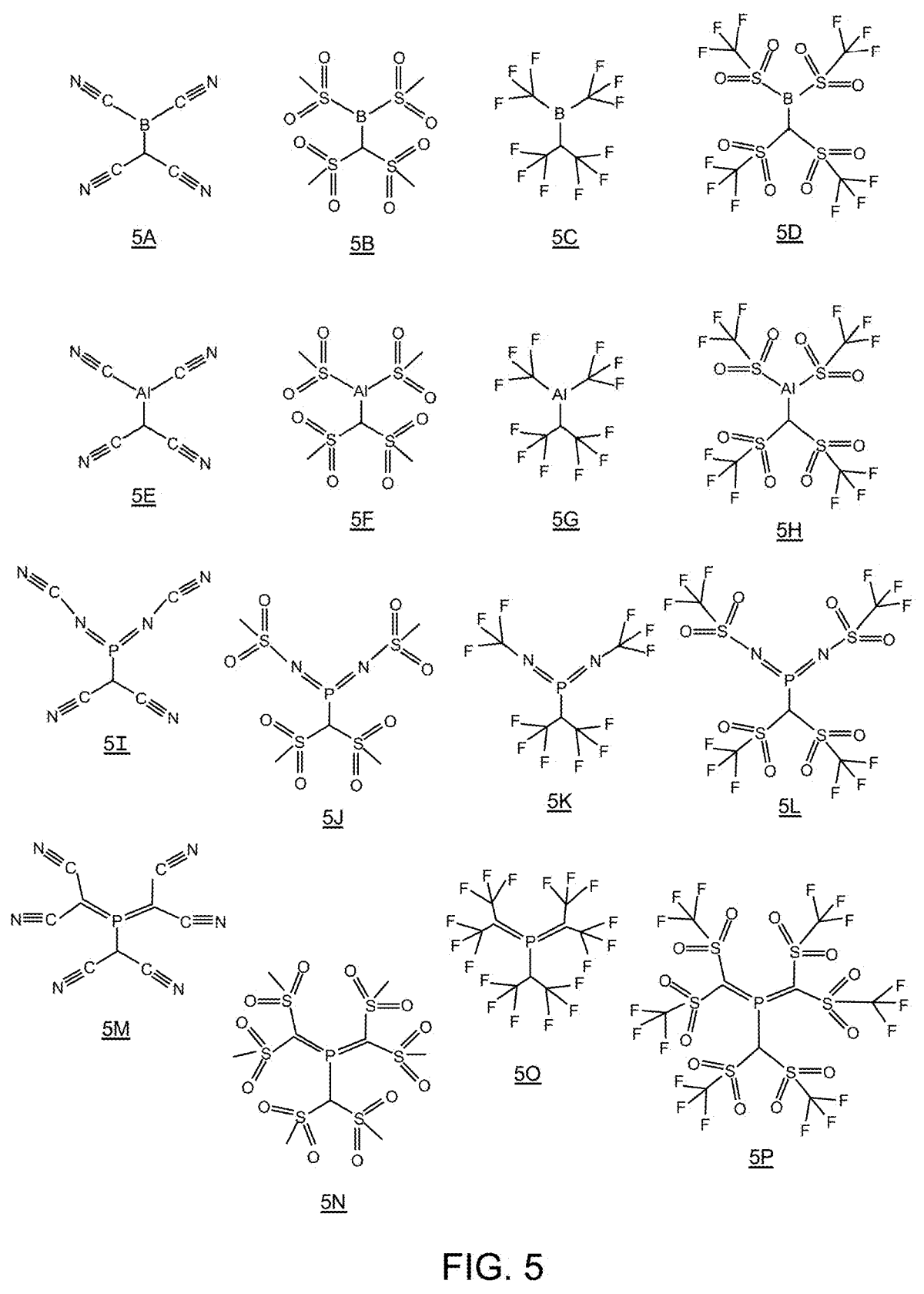

FIG. 5 displays acids 5A-5P that can be generated, upon UV exposure, by PAGs that include the PAG anions 4A-4P shown in FIG. 4, according to some embodiments of the present disclosure. The photoreaction of these PAGs can be analogous to the photoreaction depicted in FIG. 1. The illustrated PAGs are 2-(dicyanoboranyl)propanedinitrile 5A, bis(methylsulfonyl)boranyl-bis(methylsulfonyl)methane 5B, 2-(bis(trifluoromethyl)boranyl)-1,1,1,3,3,3-hexafluoropropane 5C, bis(trifluoromethylsulfonyl)boranyl-bis(trifluoromethylsulfonyl)methane 5D, 2-(dicyanoaluminyl)propanedinitrile 5E, bis(methylsulfonyl)aluminyl-bis(methylsulfonyl)methane 5F, 2-(bis(trifluoromethyl)aluminyl)-1,1,1,3,3,3-hexafluoropropane 5G, bis(trifluoromethylsulfonyl)aluminyl-bis(trifluoromethylsulfonyl)methane 5H, bis(cyanoimino)(dicyanomethyl)phosphorane 5I, bis(methylsulfonylimino)-bis(methylsulfonyl)methylphosphorane 5K, bis(trifluoromethylimino)(1,1,1,3,3,3-hexafluoroprop-2-yl)phosphorane 5J, bis(trifluoromethylsulfonylimino)-bis(trifluoromethylsulfonyl)methylphosphorane 5L, bis(dicyanomethylene)(dicyanomethyl)phosphorane 5M, bis(bis(methylsulfonyl)methylene)-bis(methylsulfonyl)methylphosphorane 5N, bis(bis(trifluoromethyl)methylene)(1,1,1,3,3,3-hexafluoroprop-2-yl)phosphorane 5O, and bis(bis(trifluoromethylsulfonyl)methylene)-bis(trifluoromethylsulfonyl)methyl-phosphorane 5P.

Ab initio gas phase simulations of proton dissociation at the PBE/DZVP level of theory were performed. The resulting proton dissociation energies determined for acids 5A-5P are, respectively, 231 kcal/mol, 278 kcal/mol, 262 kcal/mol, 225 kcal/mol, 255 kcal/mol, 300 kcal/mol, 289 kcal/mol, 252 kcal/mol, 227 kcal/mol, 264 kcal/mol, 264 kcal/mol, 244 kcal/mol, 223 kcal/mol, 266 kcal/mol, 256 kcal/mol, and 245 kcal/mol.

It is noted that the proton dissociation energy of acids generated upon UV exposure can be systematically tuned by the PAG anions' electron acceptor atom X and by the PAG anions' electron-withdrawing group R. Electronic effects can be advantageously used to devise PAGs that have fluorine-free anions and that generate, upon UV exposure, fluorine-free acids having acid-dissociation constants at least similar to that of tris(trifluoromethylsulfonyl)methane.

For example, PAGs that have a 2-(dicyanoaluminyl)propanedinitrile anion 4E can generate, upon UV exposure, acids that have a proton dissociation energy (e.g., 255 kcal/mol) similar to that of tris(trifluoromethylsulfonyl)methane (255 kcal/mol). That is, their acid-dissociation constants can be similar to that of tris(trifluoromethylsulfonyl)methane. Additionally, PAGs that have a 2-(dicyanoboranyl)propanedinitrile anion 4A can generate, upon UV exposure, acids having a proton dissociation energy (231 kcal/mol) substantially smaller than that of tris(trifluoromethylsulfonyl)methane (255 kcal/mol). That is, their acid-dissociation constants can be substantially larger than that of tris(trifluoromethylsulfonyl)methane.

PAG anions with B(III) or Al(III) electron acceptor atoms and alkylsulfonyl or fluoroalkylsulfonyl electron-withdrawing groups (e.g., methylsulfonyl or trifluoromethylsulfonyl), may be more stable when each of R1 and R4 is, for example, a methyl non-electron-withdrawing group or a cyano, tricyanoethyl, fluoro, or trifluoromethyl electron-withdrawing group. This is because the B—C, B—F, Al—C or Al—F bonds may be more stable than B—S or Al—S bonds.

Figure 6:
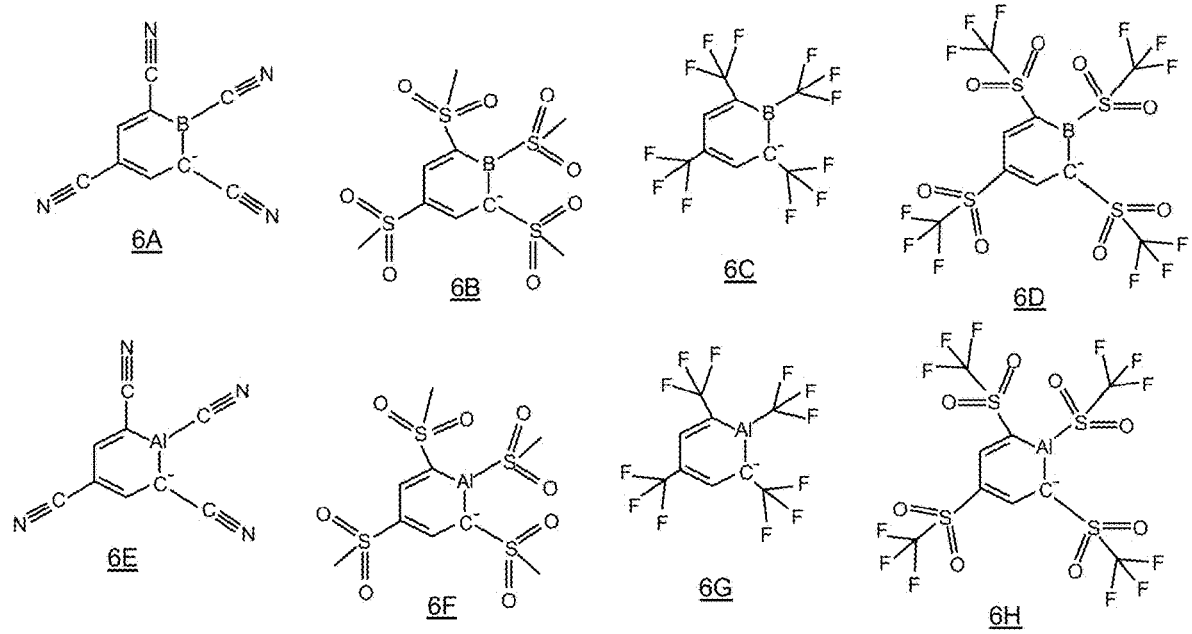
FIG. 6 illustrates chemical structure diagrams of PAG anions, according to some embodiments of the present disclosure.

FIG. 6 illustrates examples of PAG anions 6A-6H of general formula (II), according to some embodiments of the present disclosure. These PAG anions 6A-6H each have a monocyclic aromatic hydrocarbon group (a six-membered aromatic cycle). The electron acceptor atoms B(III) or Al(III) are arranged in such a way that the anion includes a covalent bond between a B(III) or Al(III) atom and a C atom that has a negative elementary charge. It is noted that, for P(V), no such heteroaromatic group can be devised. The PAG anions 6A-6H further include cyano, methylsulfonyl, trifluoromethyl, or trifluoromethylsulfonyl electron-withdrawing groups connected to the electron acceptor atoms and substituted at the ortho and para positions.

The PAG anions illustrated in FIG. 6 are 1,2,4,6-tetracyanoborinine anion 6A, 1,2,4,6-tetrakis(methylsulfonyl)borinine anion 6B, 1,2,4,6-tetrakis(trifluoromethyl)borinine anion 6C, 1,2,4,6-tetrakis(trifluoromethylsulfonyl)borinine anion 6D, 1,2,4,6-tetracyanoaluminine anion 6E, 1,2,4,6-tetrakis(methylsulfonyl)aluminine anion 6F, 1,2,4,6-tetrakis(trifluoromethyl)aluminine anion 6G, and 1,2,4,6-tetrakis(trifluoromethylsulfonyl)aluminine anion 6H.

Figure 7:
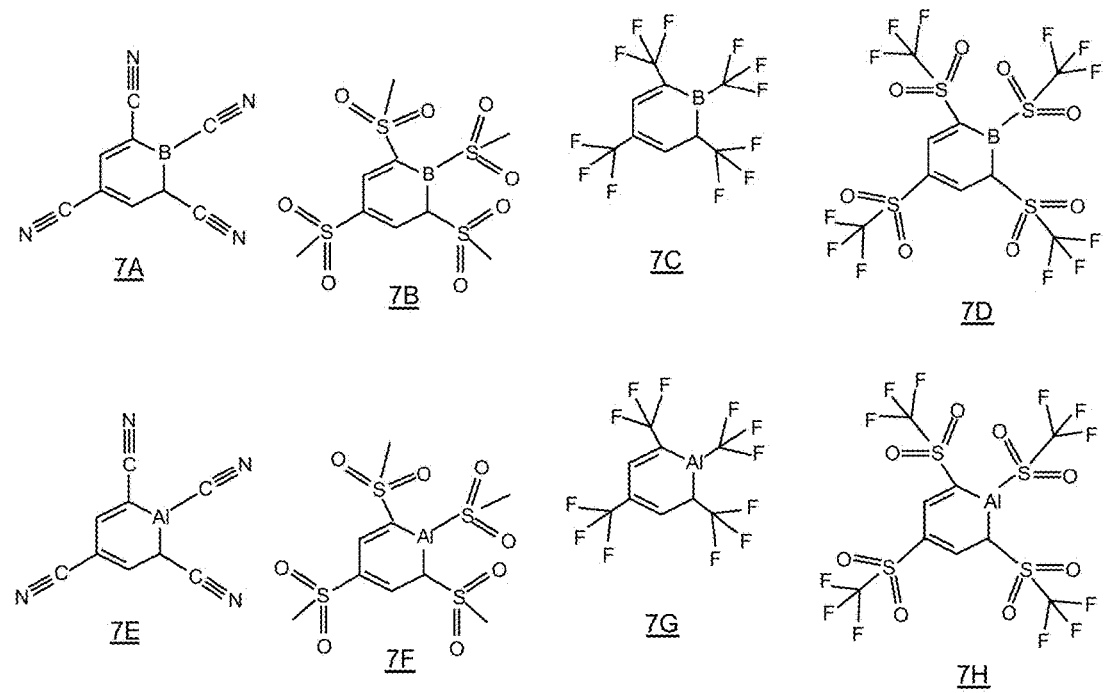
FIG. 7 illustrates chemical structure diagrams of acids that can be generated, upon UV exposure, by the PAG anions illustrated in FIG. 6, according to some embodiments of the present disclosure.

FIG. 7 illustrates acids that can be respectively generated, upon UV exposure, by PAGs 6A-6H, according to some embodiments of the present disclosure. The acids illustrated in FIG. 7 are 1,2,4,6-tetracyano-2H-borinine 7A, 1,2,4,6-tetrakis(methylsulfonyl)-2H-borinine 7B, 1,2,4,6-tetrakis(trifluoromethyl)-2H-borinine 7C, 1,2,4,6-tetrakis(trifluoromethylsulfonyl)-2H-borinine 7D, 1,2,4,6-tetracyano-2H-aluminine 7E, 1,2,4,6-tetrakis(methylsulfonyl)-2H-aluminine 7F, 1,2,4,6-tetrakis(trifluoromethyl)aluminine 7G, and 1,2,4,6-tetrakis(trifluoromethylsulfonyl)-2H-aluminine 7H.

Ab initio gas phase simulations of proton dissociation at the PBE/DZVP level of theory were performed. The resulting proton dissociation energies determined for acids 7A-7H are, respectively, 223 kcal/mol, 253 kcal/mol, 249 kcal/mol, 232 kcal/mol, 247 kcal/mol, 283 kcal/mol, 264 kcal/mol, and 246 kcal/mol.

It is noted that the proton dissociation energy of each acid 7A-7H that is generated upon UV exposure can be systematically tuned by the PAG anions' 6A-6H electron acceptor atom X and by the PAG anions' electron-withdrawing group R. It is further noted that the proton dissociation energies of the acids 7A-7H are reduced substantially compared to the "respective" alkane acid with separated R groups 5A-5H (FIG. 5). The negative elementary charges of the anions 6A-6H can be delocalized over the C atom at position 2, the B or Al atom (which is a p-orbital electron-acceptor), and now also the aromatic cycle. The in total five conjugated electrons can be delocalized over the heteroaromatic cycle, which has stabilizing π-bonds in resonance. Structural effects and electronic effects of the heteroaromatic cycles can be advantageously used to devise PAGs that have fluorine-free anions and that generate, upon UV exposure, fluorine-free acids 7A-7H that have acid-dissociation constants substantially smaller than those with separate R groups. That is, structural effects and electronic effects can be advantageously used to devise PAGs that have fluorine-free anions and that generate, upon UV exposure, fluorine-free acids with acid-dissociation constants at least similar to that of tris(trifluoromethylsulfonyl)methane.

For example, PAGs that have a 1,2,4,6-tetrakis(methylsulfonyl)borinine anion 6B can generate, upon UV exposure, acids that have a proton dissociation energy (e.g., 253 kcal/mol) substantially smaller than that of bis(methylsulfonyl)boranyl-bis(methylsulfonyl)methane 5B (278 kcal/mol) and similar to that of tris(trifluoromethylsulfonyl)methane (255 kcal/mol). That is, their acid-dissociation constants can be similar to that of tris(trifluoromethylsulfonyl)methane).

Further, PAGs that have a 1,2,4,6-tetracyanoborinine anion 6A can generate, upon UV exposure, acids having a proton dissociation energy (e.g., 223 kcal/mol) substantially smaller than those of 2-(dicyanoboranyl)propanedinitrile 5A (231 kcal/mol) and tris(trifluoromethylsulfonyl)methane (255 kcal/mol). That is, their acid-dissociation constants can be substantially larger than that of tris(trifluoromethylsulfonyl)methane).

PAG anions including B(III) or Al(III) electron acceptor atoms and alkylsulfonyl or fluoroalkylsulfonyl electron-withdrawing groups (e.g., methylsulfonyl or trifluoromethylsulfonyl) may be more stable when R1 is, for example, a methyl non-electron-withdrawing group or a cyano, tricyanoethyl, fluoro, or trifluoromethyl electron-withdrawing group. This is because B—C, B—F, Al—C, and Al—F bonds can be more stable than B—S or Al—S bonds.

Figure 8:
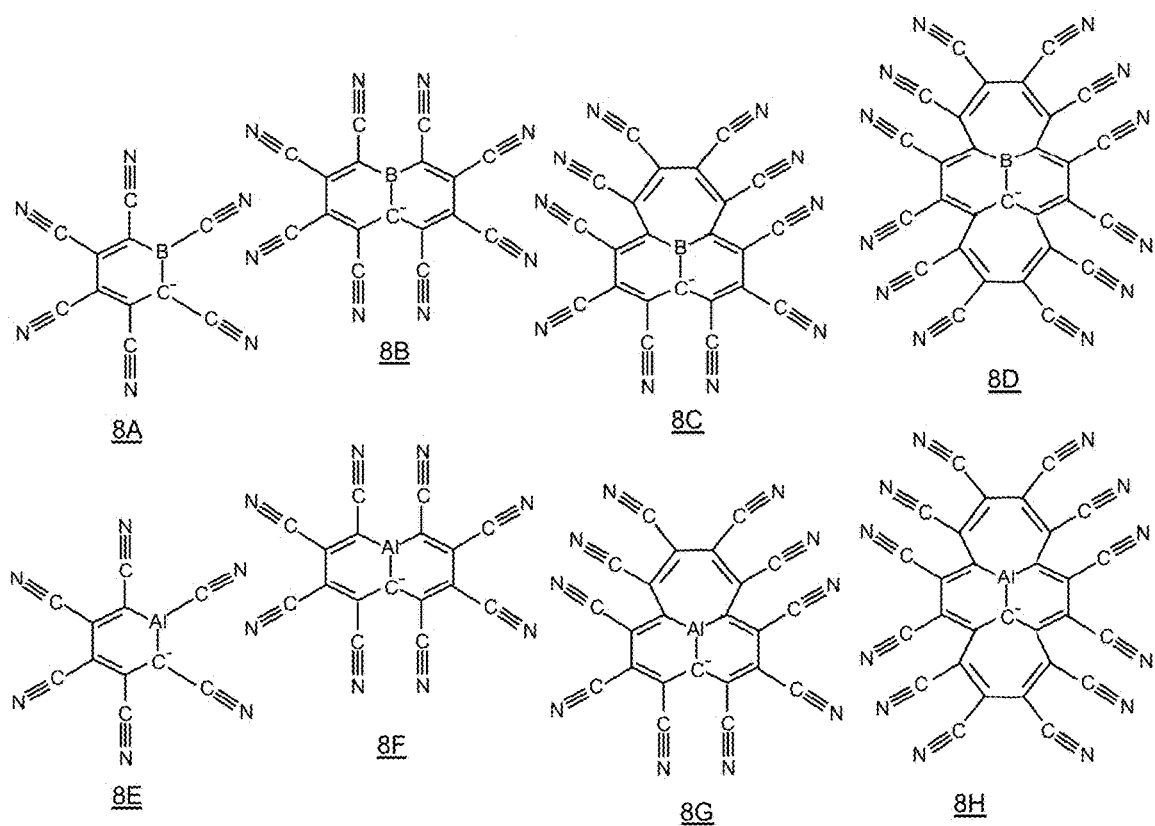
FIG. 8 illustrates chemical structure diagrams of PAG anions, according to some embodiments of the present disclosure.

FIG. 8 illustrates further examples of PAG anions 8A-8H, according to some embodiments of the present disclosure. The PAG anions illustrated in FIG. 8 are 1,2,3,4,5,6-hexacyanoborinine anion 8A, 1,2,3,4,5,6,7,8-octacyanobenzo[a]borinine anion 8B, 1,8-(1,2,3,4-tetracyanobuta[1,3]dieno)-2,3,4,5,6,7-hexacyanobenzo[a]borinine anion 8C, bis-[1,8:4,5]-(1,2,3,4-tetracyanobuta[1,3]dieno)-2,3,6,7-tetracyanobenzo[a]borinine anion 8D, 1,2,3,4,5,6-hexacyanoaluminine anion 8E, 1,2,3,4,5,6,7,8-octacyanobenzo[a]aluminine anion 8F, 1,8-(1,2,3,4-tetracyanobuta[1,3]dieno)-2,3,4,5,6,7-hexacyanobenzo[a]aluminine anion 8G, and bis-[1,8:4,5]-(1,2,3,4-tetracyanobuta[1,3]dieno)-2,3,6,7-tetracyanobenzo[a]aluminine anion 8H.

PAG anions 8A and 8E are PAG anions of general formula (II), PAG anions 8B and 8F are PAG anions of general formula (III), and PAG anions 8C, 8D, 8G, and 8H are further variants of PAG anions of general formula (III), wherein at least two adjacent R groups (e.g., R1 and R6 and/or R3 and R4 groups) are linked with each other to form an aromatic cycle such as a seven-membered aromatic cycle (8C and 8G) or two seven-membered aromatic cycles (8D and 8H). The electron acceptors B(III) or Al(III) are arranged in such a way that the anions include a covalent bond between a B(III) or Al(III) atom and a C atom with a negative elementary charge. The PAG anions 8A-8H further include cyano electron-withdrawing groups.

Figure 9:
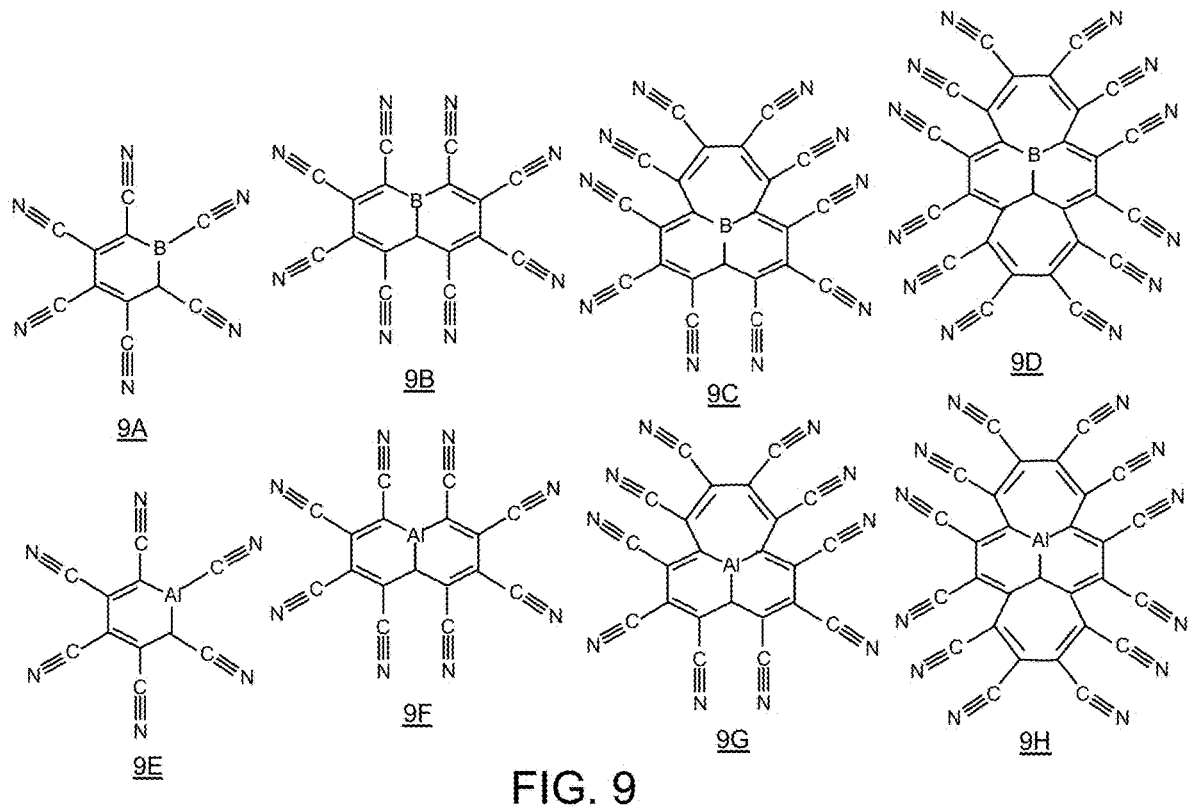
FIG. 9 illustrates chemical structure diagrams showing acids that can be generated, upon UV exposure, by the PAG anions illustrated in FIG. 8, according to some embodiments of the present disclosure.

FIG. 9 illustrates acids 9A-9H that can be respectively generated, upon UV exposure, by PAGs having the PAG anions 8A-8H illustrated in FIG. 8, according to some embodiments of the present disclosure. The acids illustrated in FIG. 9 are 1,2,3,4,5,6-hexacyano-2H-borinine 9A, 1,2,3,4,5,6,7,8-octacyano-4aH-benzo[a]borinine 9B, 1,8-(1,2,3,4-tetracyanobuta[1,3]dieno)-2,3,4,5,6,7-hexacyano-4aH-benzo[a]borinine 9C, bis-[1,8:4,5]-(1,2,3,4-tetracyanobuta[1,3]dieno)-2,3,6,7-tetracyano-4aH-benzo[a]borinine 9D, 1,2,3,4,5,6-hexacyano-2H-aluminine 9E, 1,2,3,4,5,6,7,8-octacyano-4aH-benzo[a]aluminine 9F, 1,8-(1,2,3,4-tetracyanobuta[1,3]dieno)-2,3,4,5,6,7-hexacyano-4aH-benzo[a]aluminine 9G, and bis-[1,8:4,5]-(1,2,3,4-tetracyanobuta[1,3]dieno)-2,3,6,7-tetracyano-4aH-benzo[a]aluminine 9H.

Ab initio gas phase simulations of proton dissociation at the PBE/DZVP level of theory were performed. The resulting proton dissociation energies determined for acids 9A-9H are, respectively, 207 kcal/mol, 195 kcal/mol, 193 kcal/mol, 193 kcal/mol, 232 kcal/mol, 212 kcal/mol, 208 kcal/mol, and 206 kcal/mol.

It is noted that the proton dissociation energy of the acid that is generated upon UV exposure can be systematically tuned by the PAG anions' electron acceptor atom X and by the PAG anions' aromatic cycle structure. The negative elementary charge of the anion is delocalized over the C atom at positions 2 or 4a for, respectively, -inine or benzo [a]-inine structures, the B or Al atom (which is a p-orbital electron-acceptor), and the aromatic cycles. The conjugated electrons are delocalized over the heteroaromatic cycles, which have π-bonds in resonance, which enhances the anion's stability. Structural effects and electronic effects of the hetero aromatic cycles can be advantageously used to devise PAGs that have fluorine-free anions and that generate, upon UV exposure, fluorine-free acids that have acid-dissociation constants substantially smaller than, or eventually similar to, that of PAGs with separate R groups. That is, structural effects and electronic effects can be advantageously used to devise PAGs that have fluorine-free anions and that generate, upon UV exposure, fluorine-free acids having acid-dissociation constants at least similar to that of tris(trifluoromethylsulfonyl)methane.

For example, PAGs that have a 1,2,3,4,5,6,7,8-octacyanobenzo[a]borinine anion 8B can generate, upon UV exposure, acids that have a proton dissociation energy (195 kcal/mol), which is substantially smaller than that of 1,2,3,4,5,6-hexacyano-2H-borinine 9A (207 kcal/mol). In another example, PAGs that have a 1,8-(1,2,3,4-tetracyanobuta[1,3]dieno)-2,3,4,5,6,7-hexacyanobenzo[a]borinine anion 8C can generate, upon UV exposure, acids have a proton dissociation energy (193 kcal/mol) smaller than that of 1,2,3,4,5,6,7,8-octacyano-4aH-benzo[a]borinine 9B (195 kcal/mol). Further, PAGs that have a bis-[1,8:4,5]-(1,2,3,4-tetracyanobuta[1,3]dieno)-2,3,6,7-tetracyanobenzo[a]borinine anion 8D can generate, upon UV exposure, acids having a proton dissociation energy (193 kcal/mol) similar to that of 1,8-(1,2,3,4-tetracyanobuta[1,3]dieno)-2,3,4,5,6,7-hexacyano-4aH-benzo[a]borinine 9C (193 kcal/mol). PAGs that have any of the anions depicted in FIG. 8 may generate acids that have proton dissociation energies substantially smaller than that of tris(trifluoromethylsulfonyl)methane (255 kcal/mol). That is, their acid-dissociation constants can be substantially larger than that of tris(trifluoromethylsulfonyl) methane).

Figure 10:
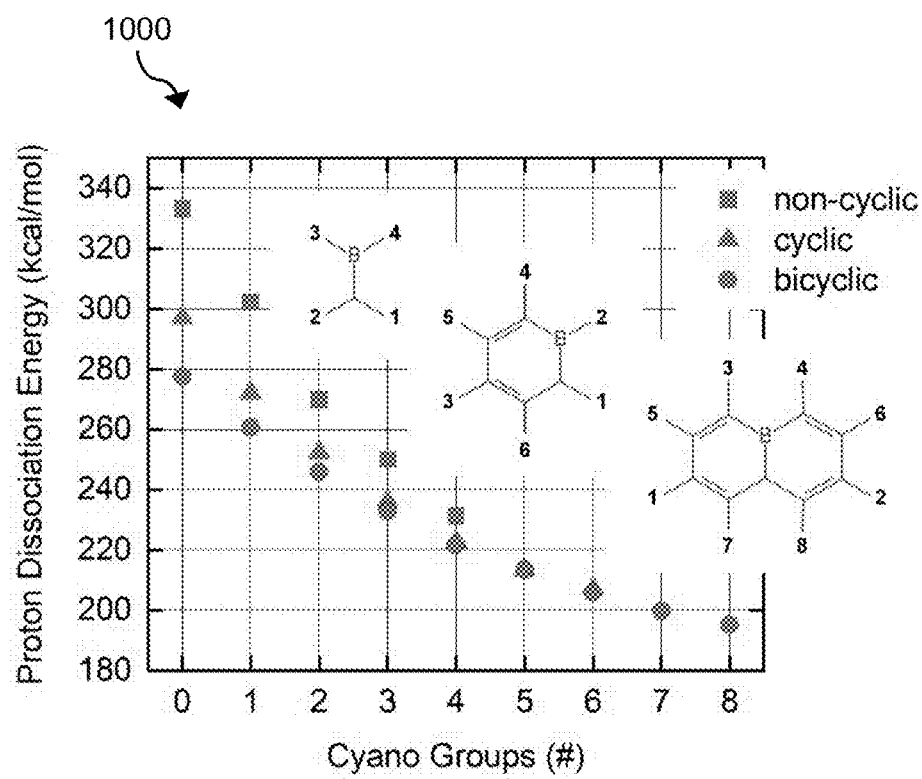
FIG. 10 illustrates proton dissociation energies of PAGs with different numbers of cyano groups, according to some embodiments of the present disclosure.

FIG. 10 is a chart 1000 illustrating relationships between the number of cyano substituents and the proton dissociation energies of acids that are generated, upon UV exposure, by PAGs including three series of PAG anions, according to some embodiments of the present disclosure. The three series of PAG anions include the heteroalkane 2-(dicyanoboranyl)propanedinitrile anion series, the heteroaromatic 1,2,3,4,5,6-hexacyanoborinine anion series, and the heteroaromatic 1,2,3,4,5,6,7,8-octacyanobenzo[a]borinine anion series. The illustrated proton dissociation energies of non-cyclic 2-(dicyanoboranyl)propanedinitrile series, monocyclic 1,2,3,4,5,6-hexacyano-2H-borinine series, and bicyclic 1,2,3,4,5,6,7,8-octacyano-4aH-benzo[a]borinine series versus number of cyano substituents are shown. The numbers in the molecule drawings indicate the sequence in which cyano groups are substituted.

The proton dissociation energies of the acids in FIG. 10, along with their substituent permutations that vary the positions of the substituents for a given number of cyano substituents are discussed in greater detail below (see FIGS. 19-21).

It is noted that the proton dissociation energy of the acid that is generated upon UV exposure can be systematically tuned by the PAG anions' structure (e.g., non-cyclic or cyclic structure) and/or by the number of the cyano groups. Structural effects and electronic effects can be advantageously used to devise PAGs that have fluorine-free anions and that generate, upon UV exposure, fluorine-free acids having acid-dissociation constants at least similar to that of tris(trifluoromethylsulfonyl)methane).

For example, PAGs that have a 2-(cyanomethylboranyl) propanedinitrile anion (three cyano groups), a 1,2-dicyanoborinine anion (two cyano groups), or a 1,2-dicyanobenzo[a]borinine anion (two cyano groups) can generate, upon UV exposure, acids that have proton dissociation energies (e.g., 250 kcal/mol, 253 kcal/mol, or 246 kcal/mol, respectively) similar to that of tris(trifluoromethylsulfonyl)methane (255 kcal/mol). That is, their acid-dissociation constants can be similar to that of tris(trifluoromethylsulfonyl)methane).

In another example, PAGs that include a 2-(dicyanoboranyl)propanedinitrile anion (four cyano groups), a 1,2,3,4,5,6-hexacyanoborinine anion (six cyano groups), or a 1,2,3,4,5,6,7,8-octacyanobenzo[a]borinine anion (eight cyano groups) can generate, upon UV exposure, acids that have proton dissociation energies (e.g., 231 kcal/mol, 207 kcal/mol, or 195 kcal/mol, respectively) substantially smaller than that of tris(trifluoromethylsulfonyl)methane (255 kcal/mol). That is, their acid-dissociation constants can be substantially larger than that of tris(trifluoromethylsulfonyl)methane.

Note that even when the PAG anion is not fully substituted with cyano groups, acids generated upon UV exposure may have the desired acid properties. Other substituents that tune additional properties may also be included. For example, substituents such as bulky aliphatic or aromatic groups (e.g., straight, branched, cyclic, or combinations thereof) that can tune an acid's diffusivity properties can still substituted. Additionally, other substituents that can tune the PAG's EUV sensitivity properties can be substituted (see below).

Figure 11:
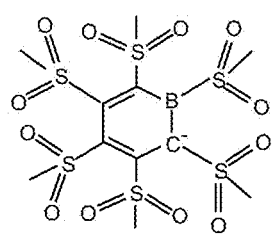
FIG. 11 illustrates chemical structure diagrams of PAG anions, according to some embodiments of the present disclosure.
Figure 11:
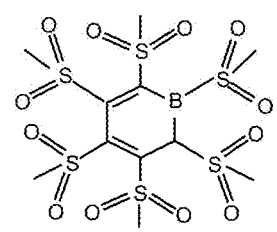
Figure 11:
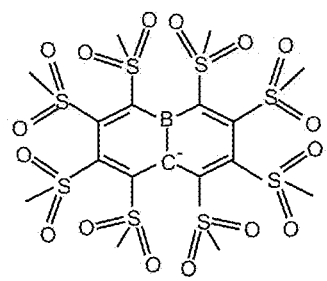

FIG. 11 illustrates examples of PAG anions, according to some embodiments of the present disclosure. Example 11A is a PAG anion of general formula (II), which is a monocyclic six-membered aromatic ring compound, and example 11B is a PAG anion of general formula (III), which is a bicyclic six-membered aromatic ring compound. The electron acceptor B(III) is arranged in such a way that the anion includes a covalent bond between a B(III) atom and a C atom with a negative elementary charge. The PAG anions 11A and 11B further include methylsulfonyl electron-withdrawing groups.

Figure 12:
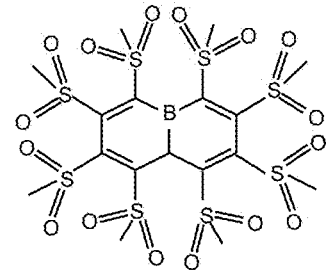
FIG. 12 illustrates chemical structure diagrams of acids that can be generated, upon UV exposure, by the PAG anions illustrated in FIG. 11, according to some embodiments of the present disclosure.

FIG. 12 illustrates acids 12A and 12B that can be respectively generated, upon UV exposure, by PAGs with anions 11A and 11B, according to some embodiments of the present disclosure. Ab initio gas phase simulations of proton dissociation at the PBE/DZVP level of theory were performed. The resulting proton dissociation energies determined for acids 12A and 12B are, respectively, 249 kcal/mol and 238 kcal/mol.

It is noted that the proton dissociation energy of the acids generated upon UV exposure can be systematically tuned by the PAG anions' aromatic cycle. The negative elementary charge of the anion is delocalized over the C atom at positions 2 or 4a for, respectively, -inine or benzo[a]-inine structures, the B atom (which is a p-orbital electron-acceptor), and now also aromatic rings. The conjugated electrons are delocalized over the heteroaromatic rings, which have stabilizing π-bonds in resonance. Structural effects and electronic effects of the heteroaromatic rings can be advantageously used to devise PAGs that have fluorine-free anions and that can generate, upon UV exposure, fluorine-free acids with acid-dissociation constants substantially smaller than, or eventually similar to, those of PAGs with separate R groups. That is, structural effects and electronic effects can be advantageously used to devise PAGs with fluorine-free anions that can generate, upon UV exposure, fluorine-free acids with acid-dissociation constants at least similar to that of tris(trifluoromethylsulfonyl)methane).

For example, PAGs that have a 1,2,3,4,5,6,7,8-octakis(methylsulfonyl)benzo[a]-borinine anion 11B generate, upon UV exposure, acids that have a proton dissociation energy of 238 kcal/mol, which is substantially smaller than that of 1,2,3,4,5,6-hexakis(methylsulfonyl)-2H-borinine 12A (249 kcal/mol) and that of tris(trifluoromethylsulfonyl)methane (255 kcal/mol). That is, their acid-dissociation constants can be substantially larger than that of tris(trifluoromethylsulfonyl)methane).

Heteroaromatic monocyclic PAG anions with a B(III) electron acceptor atom and alkylsulfonyl or fluoroalkylsulfonyl electron-withdrawing groups (e.g., methylsulfonyl or trifluoromethylsulfonyl) may be more stable when R1 is, for example, a methyl non-electron-withdrawing group or a cyano, tricyanoethyl, fluoro, or trifluoromethyl electron-withdrawing group. This is because B—C and B—F bonds may be more stable than B—S bonds.

In EUV lithography, the EUV (13.5 nm, 92 eV, soft X-ray) photon absorption can be determined by the atomic composition of the photoresist material, without considering the molecular structure. The absorption of photons in a layer of thickness d is given by $1-e^{-n\mu_a d}$, where n is the number of atoms per unit volume in the layer. To increase chemically amplified photoresists' 92-eV-photon absorption cross-section, elements that have a large absorption cross-section at this photon energy can be added to the photoresist composition. For example, the elements In, Sn, Sb, Te, Bi, Sb, and Po have a large absorption cross-section $\mu_a$ for EUV photons.

Elements that have a large absorption cross-section for photons in the EUV range can be introduced in PAG anions. These elements can include tin (Sn), antimony (Sb), and bismuth (Bi). In some embodiments, Sb and Bi may be introduced because organoantimony and organobismuth compounds generally have a toxicity advantage over organotin compounds. For example, the mean lethal dose LD50 of triphenyltin is one to two orders of magnitude lower than that of triphenylantimony and triphenylbismuth. Moreover, bismuth compounds generally have a cost advantage.

Figure 13:
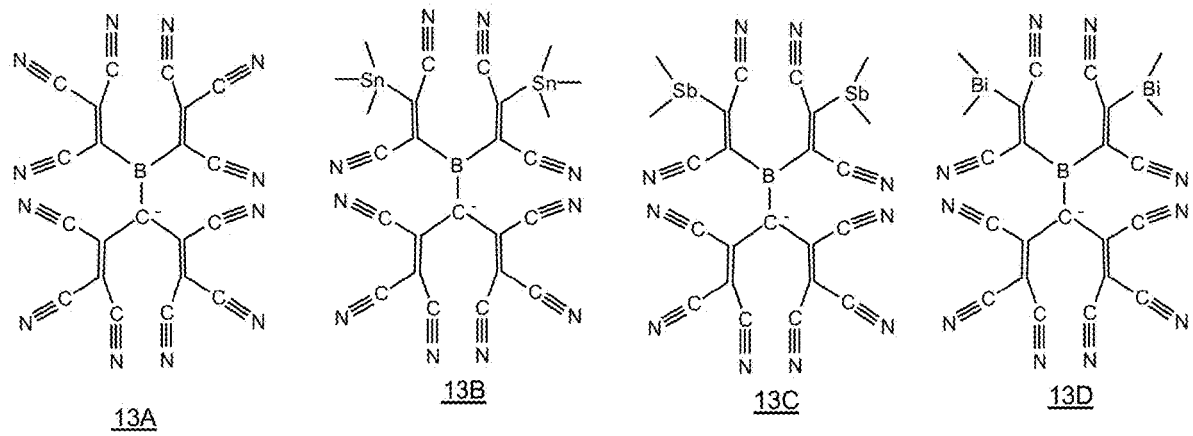
FIG. 13 illustrates chemical structure diagrams of PAG anions, according to some embodiments of the present disclosure.

FIG. 13 illustrates examples of heteroalkene methylborane PAG anions 13A-13D that may be used for EUV lithography, according to some embodiments of the present disclosure. The illustrated PAG anions 13A-13D include bis(2-(dimethylbismuthyl)-1,2-dicyanoethen-1-yl)-(1,1,2,4,5,5-hexacyanopent-1,4-dien-3-yl)borane anion 13D. The electron acceptor atom B(III) is arranged in such a way that the anions each include a covalent bond between a B(III) atom and a C atom with a negative elementary charge. The PAG anions 13A-13D further include tricyanoethyl electron-withdrawing groups. These electron-withdrawing groups each have stannyl-, antimonyl-, or bismuthyl-group substituents.

The PAG anions illustrated in FIG. 13 are bis(1,2,2-tricyanoethen-1-yl)-(1,1,2,4,5,5-hexacyanopent-1,4-dien-3-yl)borane anion 13A, bis(2-(trimethylstannyl)-1,2-dicyanoethen-1-yl)-(1,1,2,4,5,5-hexacyanopent-1,4-dien-3-yl)borane anion 13B, bis(2-(dimethylantimonyl)-1,2-dicyanoethen-1-yl)-(1,1,2,4,5,5-hexacyanopent-1,4-dien-3- yl)borane anion 13C, and bis(2-(dimethylbismuthyl)-1,2-dicyanoethen-1-yl)-(1,1,2,4,5,5-hexacyanopent-1,4-dien-3-yl)borane anion 13D.

Figure 14:
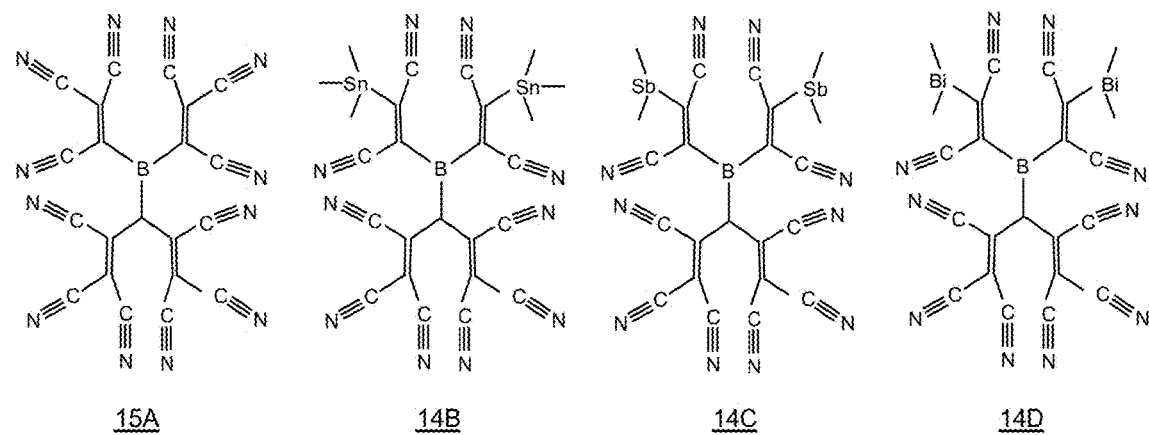
FIG. 14 illustrates chemical structure diagrams of acids that can be generated, upon UV exposure, by the PAG anions illustrated in FIG. 13, according to some embodiments of the present disclosure.

FIG. 14 illustrates acids 14A-14D that can be generated, upon UV exposure, by PAGs with the PAG anions 13A-13D illustrated in FIG. 13, according to some embodiments of the present disclosure. These acids are bis(1,2,2-tricyanoethen-1-yl)-(1,1,2,4,5,5-hexacyanopent-1,4-dien-3-yl)borane 14A, bis(2-(trimethylstannyl)-1,2-dicyanoethen-1-yl)-(1,1,2,4,5,5-hexacyanopent-1,4-dien-3-yl)borane 14B, bis(2-(dimethylantimonyl)-1,2-dicyanoethen-1-yl)-(1,1,2,4,5,5-hexacyanopent-1,4-dien-3-yl)borane 14C, and bis(2-(dimethylbismuthyl)-1,2-dicyanoethen-1-yl)-(1,1,2,4,5,5-hexacyanopent-1,4-dien-3-yl)borane 14D.

Ab initio gas phase simulations of proton dissociation at the PBE/DZVP level of theory were performed. The resulting proton dissociation energies determined for the acids 14A-14D are, respectively, 226 kcal/mol, 238 kcal/mol, 236 kcal/mol, and 238 kcal/mol.

It is noted that the proton dissociation energy of the acid that is generated upon UV exposure can be essentially independent of which of stannyl-, antimonyl-, and bismuthyl-group substituent is used. A tricyanoethyl electron-withdrawing group R may be preferred over a cyano electron-withdrawing group R. The proton dissociation energies of the acids having stannyl-, antimonyl-, and bismuthyl-group substituents can be in line with the proton dissociation energy of the unsubstituted bis(2-methyl-1,2-dicyanoethen-1-yl)-(1,1,2,4,5,5-hexacyanopent-1,4-dien-3-yl)borane. Substituents with improved photon absorption cross-sections at 92 eV can be advantageously used to devise PAGs that have fluorine-free anions and that generate, upon UV exposure, fluorine-free acids with acid-dissociation constants at least similar to that of tris(trifluoromethylsulfonyl)methane.

For example, PAGs that have a bis(2-(dimethylbismuthyl)-1,2-dicyanoethen-1-yl)-(1,1,2,4,5,5-hexacyanopent-1,4-dien-3-yl)borane anion 13D can generate, upon UV exposure, acids that have a proton dissociation energy (e.g., 238 kcal/mol) still substantially smaller than that of tris(trifluoromethylsulfonyl)methane (255 kcal/mol). That is, the acid-dissociation constants of these acids (e.g., 14D) may be substantially larger than that of tris(trifluoromethylsulfonyl)methane).

Figure 15:
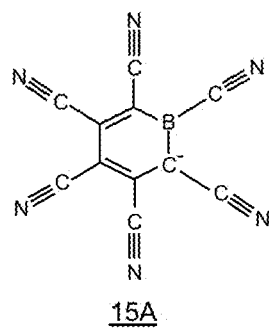
FIG. 15 illustrates chemical structure diagrams of PAG anions, according to some embodiments of the present disclosure.
Figure 15:
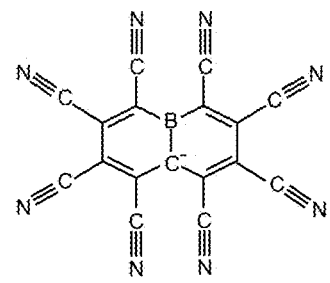
Figure 15:
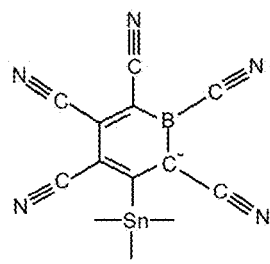
Figure 15:
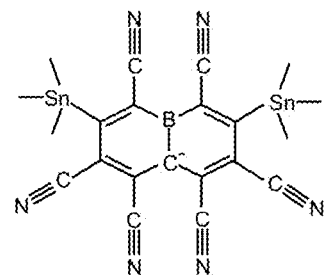
Figure 15:
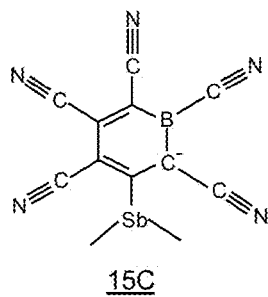
Figure 15:
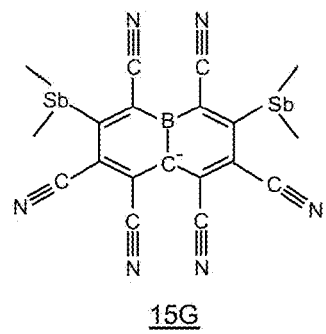
Figure 15:
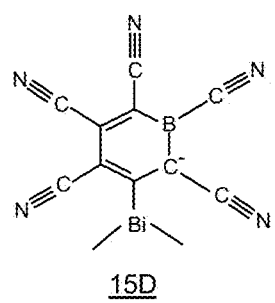
Figure 15:
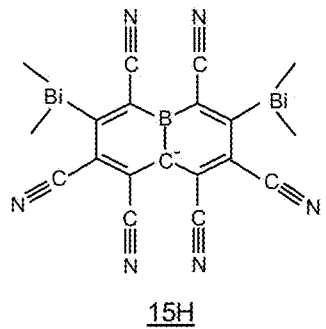

FIG. 15 illustrates additional examples of PAG anions 15A-15H that may be used for EUV lithography, according to some embodiments of the present disclosure. Anions 15A-15D are PAG anions of formula (II) and anions 15E-15H are PAG anions of formula (III). The electron acceptor atom B(III) is arranged in such a way that the anions each include a covalent bond between a B(III) atom and a C atom with a negative elementary charge. The PAG anions 15A-15H further include cyano electron-withdrawing groups. PAG anions 15B-15D and 15F-15H also include stannyl-, antimonyl-, or bismuthyl-group substituents.

The PAG anions illustrated in FIG. 15 are 1,2,3,4,5,6-hexacyanoborinine anion 15A, 1,2,4,5,6-pentacyano-3-(trimethylstannyl)borinine anion 15B, 1,2,4,5,6-pentacyano-3-(dimethylantimonyl)borinine anion 15C, 1,2,4,5,6-pentacyano-3-(dimethylbismuthyl)borinine anion 15D, 1,2,3,4,5,6,7,8-octacyanobenzo[a]borinine anion 15E, 1,3,4,5,6,8-hexacyano-2,7-bis(trimethylstannyl)benzo[a]borinine anion 15F, 1,3,4,5,6,8-hexacyano-2,7-bis(dimethylantimonyl)benzo[a]borinine anion 15G, and 1,3,4,5,6,8-hexacyano-2,7-bis(dimethylbismuthyl)benzo[a]borinine anion 15H.

Figure 16:
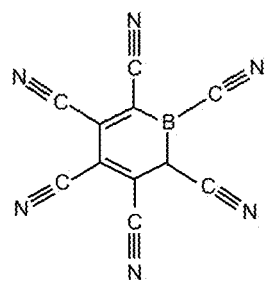
FIG. 16 illustrates chemical structure diagrams showing acids that can be generated, upon UV exposure, by the PAG anions illustrated in FIG. 15, according to some embodiments of the present disclosure.
Figure 16:
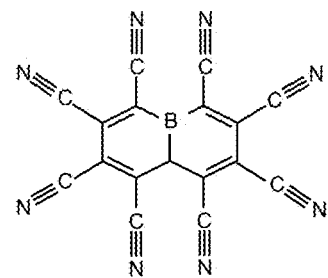
Figure 16:
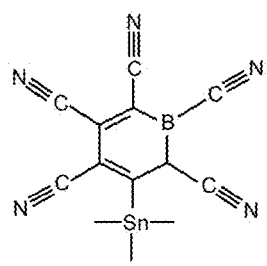
Figure 16:
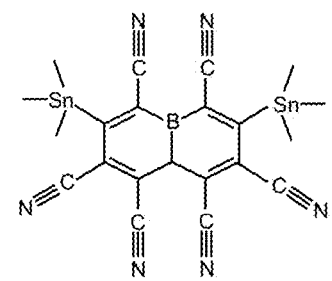
Figure 16:
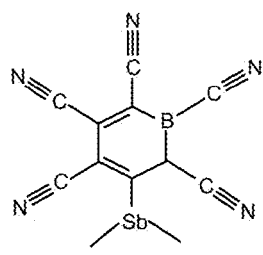
Figure 16:
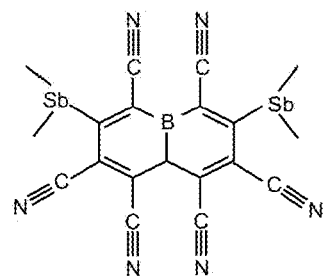
Figure 16:
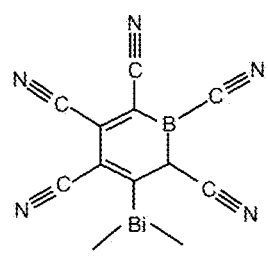
Figure 16:
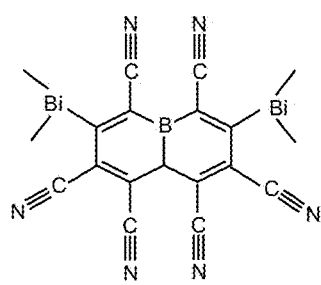

FIG. 16 illustrates acids 16A-16H that can be generated, upon UV exposure, by PAG anions 15A-15H, according to some embodiments of the present disclosure. These acids include 1,2,3,4,5,6-hexacyanoborinine 16A, 1,2,4,5,6-pentacyano-3-(trimethylstannyl)borinine 16B, 1,2,4,5,6-pentacyano-3-(dimethylantimonyl)borinine 16C, 1,2,4,5,6-pentacyano-3-(dimethylbismuthyl)borinine 16D, 1,2,3,4,5,6,7,8-octacyanobenzo[a]borinine 16E, 1,3,4,5,6,8-hexacyano-2,7-bis(trimethylstannyl)benzo[a]borinine 16F, 1,3,4,5,6,8-hexacyano-2,7-bis(dimethylantimonyl)benzo[a]borinine 16G, and 1,3,4,5,6,8-hexacyano-2,7-bis(dimethylbismuthyl)benzo[a]borinine 16H.

Ab initio gas phase simulations of proton dissociation at the PBE/DZVP level of theory were performed. The resulting proton dissociation energies determined for the acids 16A-16H illustrated in FIG. 16 are, respectively, 207 kcal/mol, 223 kcal/mol, 224 kcal/mol, 224 kcal/mol, 195 kcal/mol, 220 kcal/mol, 219 kcal/mol, and 219 kcal/mol.

It is noted that the proton dissociation energy of the acid generated upon UV exposure can be essentially independent of which of stannyl-, antimonyl-, and bismuthyl-group substituent is used. The proton dissociation energies of the acids with stannyl-, antimonyl-, and bismuthyl-group substituents can be in line with the proton dissociation energies of the unsubstituted acids 1,2,4,5,6-pentacyano-2H-borinine and 1,3,4,5,6,8-hexacyano-4aH-benzo[a]borinine. Substituents with improved photon absorption cross-sections at 92 eV may be advantageously used to devise PAGs that have fluorine-free anions and that generate, upon UV exposure, fluorine-free acids having acid-dissociation constants at least similar to that of tris(trifluoromethylsulfonyl)methane.

For example, PAGs that have a 1,2,4,5,6-pentacyano-3-(dimethylbismuthyl)borinine anion 15D or a 1,3,4,5,6,8-hexacyano-2,7-di(dimethylbismuthyl)benzo[a]borinine anion 15H can generate, upon UV exposure, acids that have proton dissociation energies (e.g., 224 kcal/mol or 219 kcal/mol, respectively) substantially smaller than that of tris(trifluoromethylsulfonyl)methane (255 kcal/mol). That is, the acid-dissociation constants of acids 16D and 16H can be substantially larger than that of tris(trifluoromethylsulfonyl)methane).

In some embodiments, examples of PAG anions for chemically amplified photoresists for EUV lithography can include a bis(trimethylstannyldicyanoethen-1-yl)-(1,1,2,4,5,5-hexacyanopent-1,4-dien-3-yl)borane anion, bis(dimethylantimonyldicyanoethen-1-yl)-(1,1,2,4,5,5-hexacyanopent-1,4-dien-3-yl)borane anion, bis(dimethylbismuthyldicyanoethen-1-yl)-(1,1,2,4,5,5-hexacyanopent-1,4-dien-3-yl)borane anion, bis(triphenylstannyldicyanoethen-1-yl)-(1,1,2,4,5,5-hexacyanopent-1,4-dien-3-yl)borane anion, bis(diphenylantimonyldicyanoethen-1-yl)-(1,1,2,4,5,5-hexacyanopent-1,4-dien-3-yl)borane anion, bis(diphenylbismuthyldicyanoethen-1-yl)-(1,1,2,4,5,5-hexacyanopent-1,4-dien-3-yl)borane anion, pentacyano-(trimethylstannyl)borinine anion, pentacyano-(dimethylantimonyl)borinine anion, pentacyano-(dimethylbismuthyl)borinine anion, pentacyano-(triphenylstannyl)borinine anion, pentacyano-(diphenylantimonyl)borinine anion, pentacyano-(diphenylbismuthyl)borinine anion, hexacyano-bis(trimethylstannyl)benzo[a]borinine anion, hexacyano-bis(dimethylantimonyl)benzo[a]borinine anion, hexacyano-bis(dimethylbismuthyl)benzo[a]borinine anion, hexacyano-bis(triphenylstannyl)benzo[a]borinine anion, hexacyano-bis(diphenylantimonyl)benzo[a]borinine anion, and/or hexacyano-bis(diphenylbismuthyl)benzo[a]borinine anion.

Figure 17:
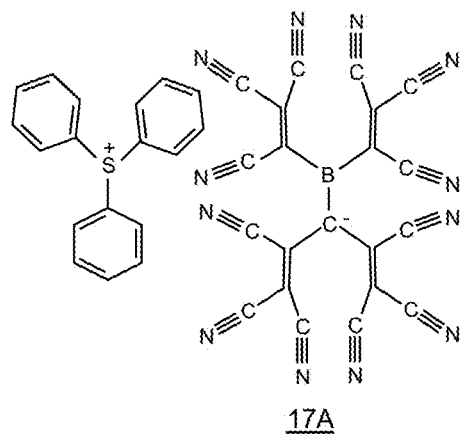
FIG. 17 illustrates chemical structure diagrams of example PAGs, according to some embodiments of the present disclosure.
Figure 17:
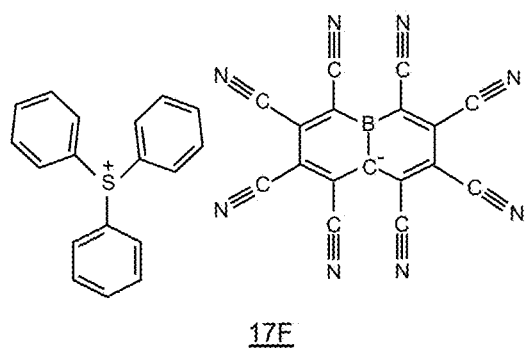
Figure 17:
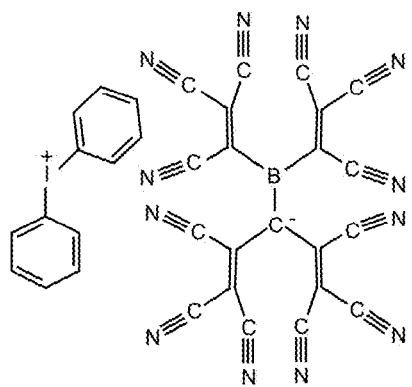
Figure 17:
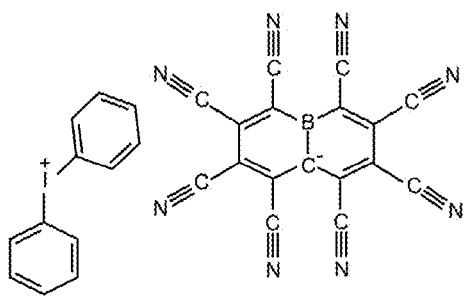
Figure 17:
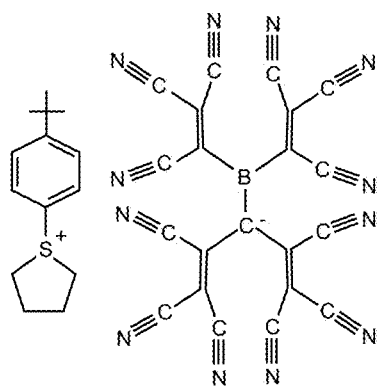
Figure 17:
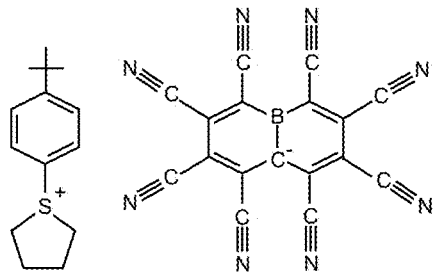

FIG. 17 illustrates examples of PAGs that include PAG anions and known cations, according to some embodiments of the present disclosure. PAGs with the aforementioned conjugate bases or photoacid generator anions may also include cations such as triphenylsulfonium, diphenyliodonium, phenylthiolanium, or derivatives thereof. Examples of PAGs that include combinations of PAG anions disclosed herein and known PAG cations can include triphenylsulfonium bis(1,2,2-tricyanoethen-1-yl)-(1,1,2,4,5,5-hexacyanopent-1,4-dien-3-yl)borane 17A, triphenylsulfonium 1,2,3,4,5,6,7,8-octacyanobenzo[a]borinine 17B, diphenyliodonium bis(1,2,2-tricyanoethen-1-yl)-(1,1,2,4,5,5-hexacyanopent-1,4-dien-3-yl)borane 17C, diphenyliodonium 1,2,3,4,5,6,7,8-octacyanobenzo[a]borinine 17D, phenylthiolanium bis(1,2,2-tricyanoethen-1-yl)-(1,1,2,4,5,5-hexacyanopent-1,4-dien-3-yl)borane 17E, and phenylthiolanium 1,2,3,4,5,6,7,8-octacyanobenzo[a]borinine 17F; these PAGs generate, upon UV exposure, acids that have an acid-dissociation constant higher than that of tris(trifluoromethylsulfonyl)methane.

Figure 18:
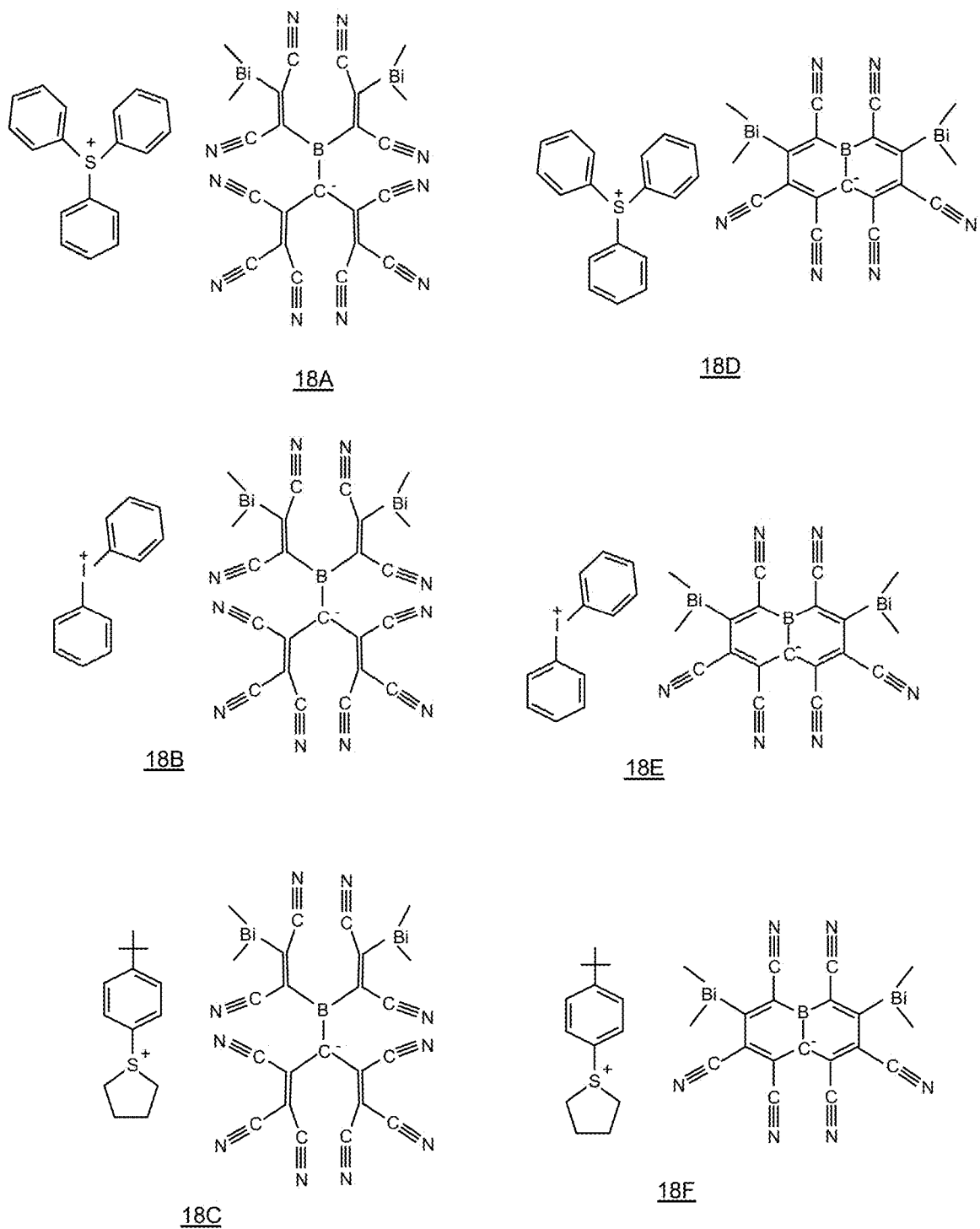
FIG. 18 illustrates chemical structure diagrams of example PAGs that may be used in EUV lithography, according to some embodiments of the present disclosure.

FIG. 18 illustrates further examples of PAGs that include PAG anions combined with known cations, and which may be used in EUV lithography, according to some embodiments of the present disclosure. These PAGs 18A-18F can include combinations of PAG anions disclosed herein and known PAG cations such as triphenylsulfonium, diphenyliodonium, phenylthiolanium, and their derivatives. The illustrated PAGs include triphenylsulfonium bis(2-(dimethylbismuthyl)-1,2-dicyanoethen-1-yl)-(1,1,2,4,5,5-hexacyanopent-1,4-dien-3-yl)borane 18A, triphenylsulfonium 1,3,4,5,6,8-hexacyano-2,7-di(dimethylbismuthyl)benzo[a]borinine 18B, diphenyliodonium bis(2-(dimethylbismuthyl)-1,2-dicyanoethen-1-yl)-(1,1,2,4,5,5-hexacyanopent-1,4-dien-3-yl)borane 18C, diphenyliodonium 1,3,4,5,6,8-hexacyano-2,7-di(dimethylbismuthyl)-benzo[a]borinine 18D, phenylthiolanium bis(2-(dimethylbismuthyl)-1,2-dicyanoethen-1-yl)-(1,1,2,4,5,5-hexacyanopent-1,4-dien-3-yl)borane 18E, and phenylthiolanium 1,3,4,5,6,8-hexacyano-2,7-di(dimethylbismuthyl)-benzo[a]borinine 18F. These PAGs can generate, upon UV exposure, acids that have an acid-dissociation constant higher than that of tris(trifluoromethylsulfonyl)methane.

Figure 19:
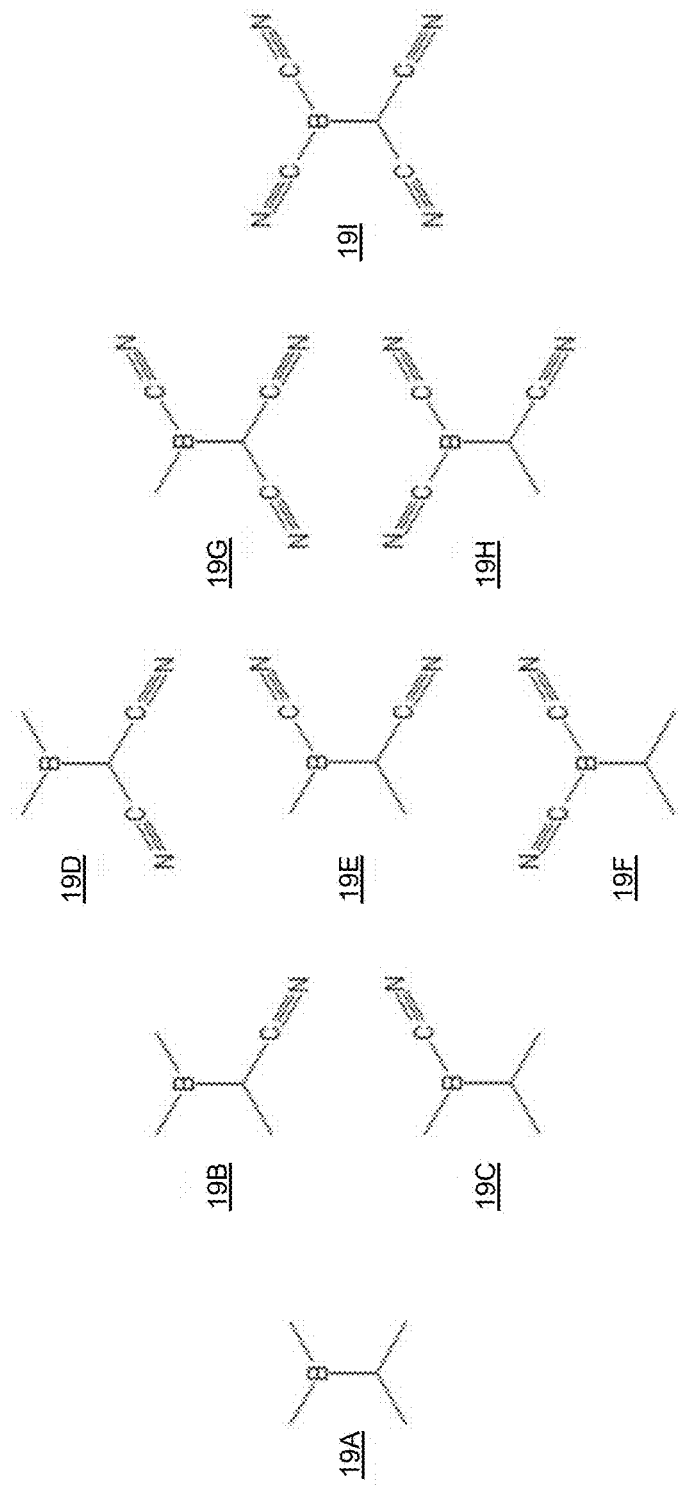
FIG. 19 illustrates a heteroalkane acid series, according to some embodiments of the present disclosure.

FIG. 19 illustrates a heteroalkane acid series, according to some embodiments of the present disclosure. The illustrated acids include 2-(dimethylboranyl)propane 19A, 2-(dimethylboranyl)propanenitrile 19B, 2-(methylcyanoboranyl)propane 19C, 2-(dimethylboranyl)propanedinitrile 19D, 2-(methylcyanoboranyl)propanenitrile 19E, 2-(dicyanoboranyl)propane 19F, 2-(methylcyanoboranyl)propanedinitrile 19G, 2-(dicyanoboranyl)propanenitrile 19H, and 2-(dicyanoboranyl)propanedinitrile 19I.

Ab initio gas phase simulation of proton dissociation at the PBE/DZVP level of theory were performed. The resulting proton dissociation energies determined for the acids 19A-19I depicted in FIG. 19 are, respectively, 333 kcal/mol, 302 kcal/mol, 306 kcal/mol, 270 kcal/mol, 276 kcal/mol, 278 kcal/mol, 250 kcal/mol, 255 kcal/mol, and 231 kcal/mol. It is noted that the proton-dissociation energy difference of, for example, 2-(dimethylboranyl)propanenitrile 19B (302 kcal/mol) and 2-(methylcyanoboranyl)propane 19C (306 kcal/mol) or of 2-(methylcyanoboranyl)propanedinitrile 19G (250 kcal/mol) and 2-(dicyanoboranyl)propanenitrile 19H (255 kcal/mol), is about −4 kcal/mol.

Cyano groups may have a more pronounced stabilization effect on the anion when attached to the C atom than when attached to the B atom. The reason for this is that when the cyano group is attached to the C atom, the anion's negative charge is delocalized over the heteroalkene group and the cyano group, while when the cyano group is attached to the B atom, the cyano group has a more indirect effect on the anion's negative charge delocalization. The cyano group influences the polarization of the B atom.

Figure 20:
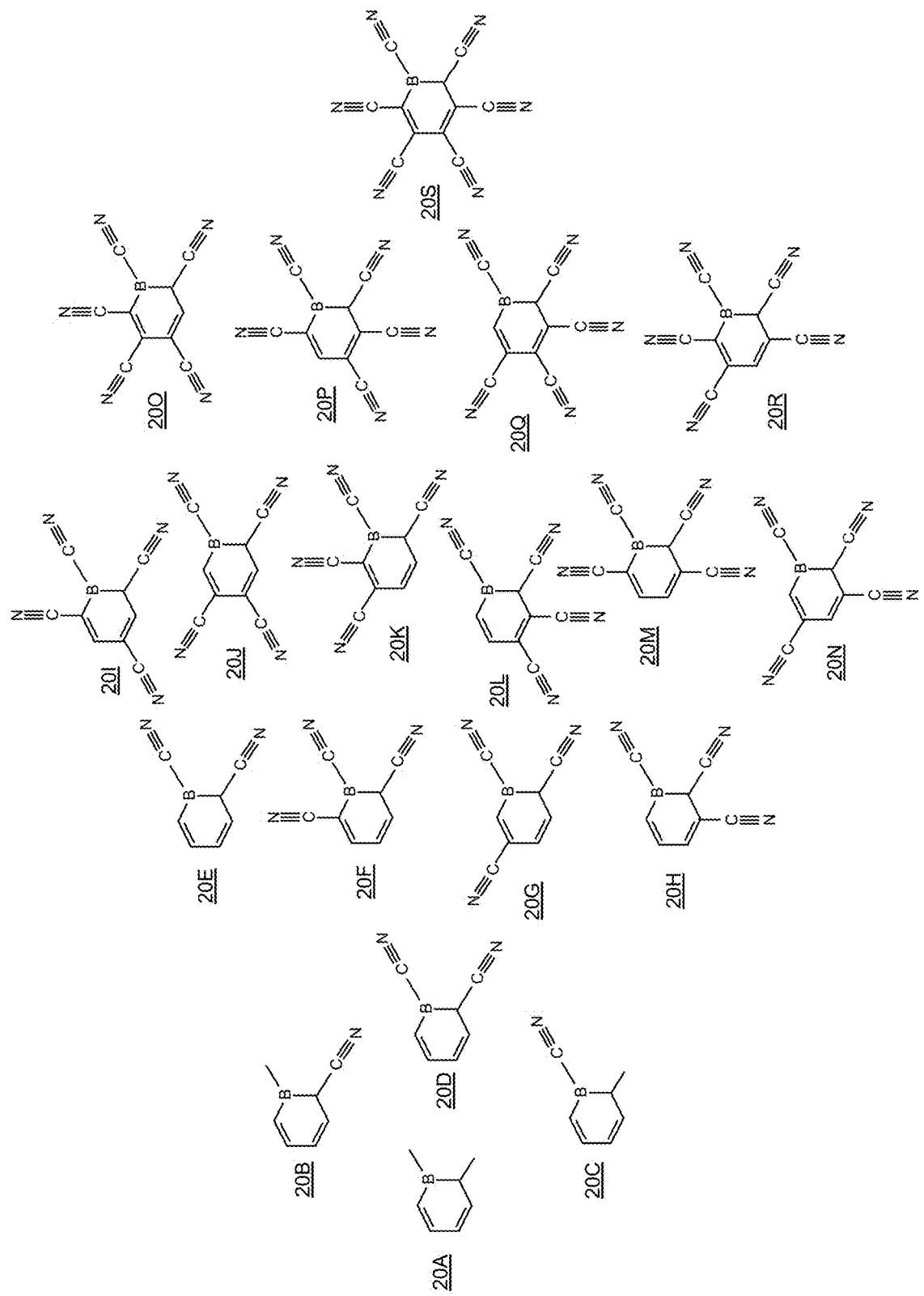
FIG. 20 illustrates a heteroaromatic monocyclic acid series, according to some embodiments of the present disclosure.

FIG. 20 illustrates a heteroaromatic monocyclic acid series, according to some embodiments of the present disclosure. These acids include 1,2-dimethyl-2H-borinine 20A, 1-methyl-2-cyano-2H-borinine 20B, 2-methyl-1-cyano-2H-borinine 20C, 1,2-dicyano-2H-borinine 20D, 1,2,4-tricyano-2H-borinine 20E, 1,2,6-tricyano-2H-borinine 20F, 1,2,5-tricyano-2H-borinine 20G, 1,2,3-tricyano-2H-borinine 20H, 1,2,4,6-tetracyano-2H-borinine 19I, 1,2,4,5-tetracyano-2H-borinine 19J, 1,2,5,6-tetracyano-2H-borinine 20K, 1,2,3,4-tetracyano-2H-borinine 20L, 1,2,3,6-tetracyano-2H-borinine 20M, 1,2,3,5-tetracyano-2H-borinine 20N, 1,2,4,5,6-pentacyano-2H-borinine 20O, 1,2,3,4,6-pentacyano-2H-borinine 20P, 1,2,3,4,5-pentacyano-2H-borinine 20Q, 1,2,3,5,6-pentacyano-2H-borinine 20R, and 1,2,3,4,5,6-hexacyano-2H-borinine 20S.

Ab initio gas phase simulations of proton dissociation at the PBE/DZVP level of theory were performed to find proton dissociation energies of acids 20A-20S. These proton dissociation energies are, respectively, 297 kcal/mol, 272 kcal/mol, 276 kcal/mol, 253 kcal/mol, 236 kcal/mol, 237 kcal/mol, 238 kcal/mol, 241 kcal/mol, 223 kcal/mol, 224 kcal/mol, 226 kcal/mol, 227 kcal/mol, 227 kcal/mol, 228 kcal/mol, 214 kcal/mol, 215 kcal/mol, 217 kcal/mol, 217 kcal/mol, and 207 kcal/mol.

It is noted that the proton-dissociation energy difference of, for example, 1-methyl cyano-2H-borinine 19B (272 kcal/mol) and 2-methyl-1-cyano-2H-borinine 19C (276 kcal/mol) or of 1,2,4,5,6-pentacyano-2H-borinine 20O (214 kcal/mol) and 1,2,3,5,6-pentacyano-2H-borinine 20R (217 kcal/mol) is about −4 kcal/mol. Cyano groups can have a more pronounced stabilizing effect on an anion when attached at the positions 2, 4, and/or 6 than when attached at positions 1, 3, and/or 5. The reason for this is that when the cyano group is attached at the positions 2, 4, and/or 6, the anion's negative charge can be delocalized over the heteroaryl cycle and the cyano group, while when the cyano group is attached at positions 1, 3, and/or 5, the cyano group has a more indirect effect on the anion's negative charge delocalization. The cyano group influences the polarization of the heteroaryl cycle.

Figure 21:
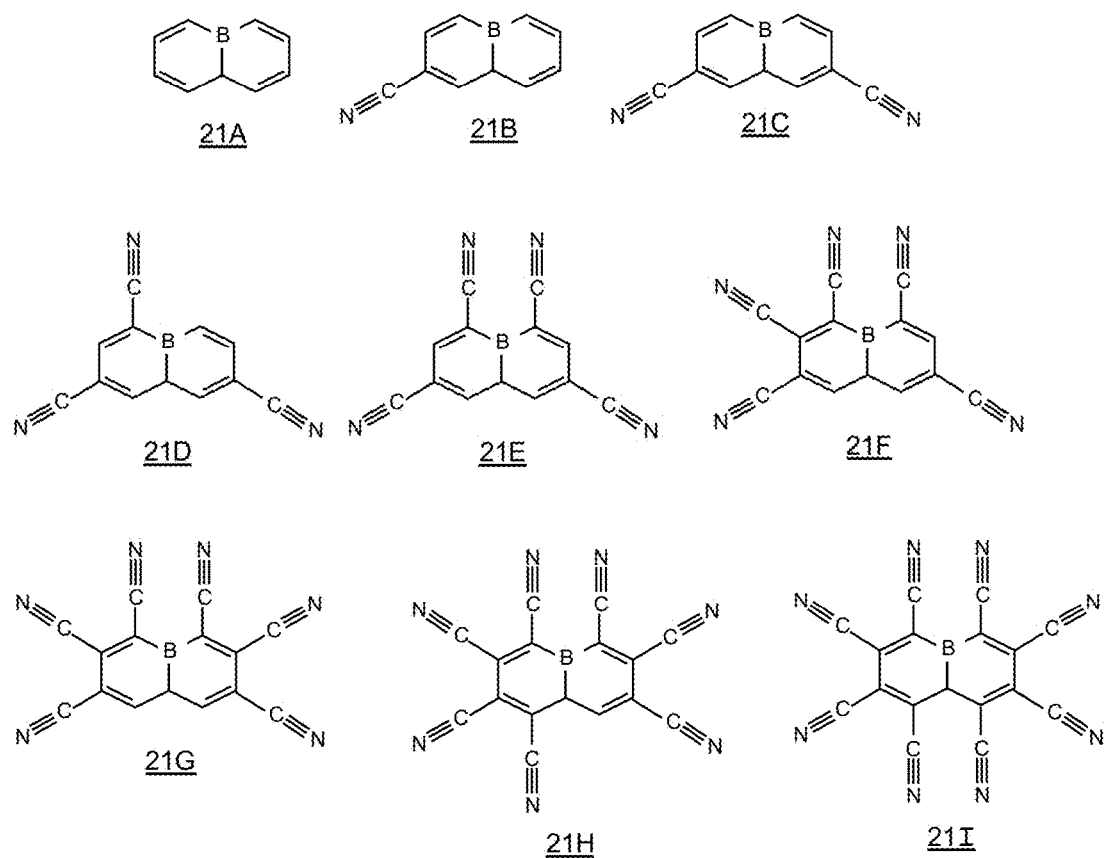
FIG. 21 illustrates a heteroaromatic bicyclic acid series, according to some embodiments of the present disclosure.

FIG. 21 illustrates a heteroaromatic bicyclic acid series, according to some embodiments of the present disclosure. These acids include 4aH-benzo[a]borinine 21A, 3-cyano-4aH-benzo[a]borinine 21B, 3,6-dicyano-4aH-benzo[a]borinine 21C, 1,3,6-tricyano-4aH-benzo[a]borinine 21D, 1,3,6,8-tetracyano-4aH-benzo[a]borinine 21E, 1,2,3,6,8-pentacyano-4aH-benzo[a]borinine 21F, 1,2,3,6,7,8-hexacyano-4aH-benzo[a]borinine 21G, 1,2,3,4,6,7,8-heptacyano-4aH-benzo[a]borinine 21H, and 1,2,3,4,5,6,7,8-octacyano-4aH-benzo[a]borinine 21I.

Ab initio gas phase simulations of proton dissociation at the PBE/DZVP level of theory were carried out to determine the proton dissociation energies of acids 21A-21I. The resulting proton dissociation energies determined for the acids 21A-21I are, respectively, 278 kcal/mol, 261 kcal/mol, 246 kcal/mol, 233 kcal/mol, 222 kcal/mol, 214 kcal/mol, 206 kcal/mol, 200 kcal/mol, and 195 kcal/mol.

In some embodiments, at least one group R1, R2, R3, R4, R5, or R6 of the PAG anion of formula (I), formula (II), or formula (III) has a trialkylstannyl-, a triarylstannyl-, a dialkylantimonyl-, a diarylantimonyl, a dialkylbismuthyl-, and/or a diarylbismuthyl group. Examples of these groups can include a trimethylstannyl-, a triphenylstannyl-, a dimethylantimonyl-, a diphenylantimonyl, a dimethylbismuthyl-, and a diphenylbismuthyl group.

In further embodiments, at least one group R1, R2, R3, R4, R5, or R6 of the PAG anion of formula (I), formula (II), or formula (III) is substituted with a trialkylstannyl-, a triarylstannyl-, a dialkylantimonyl-, a diarylantimonyl, a dialkylbismuthyl-, or a diarylbismuthyl group. For example, R1, R2, R3, R4, R5, and/or R6 can be a trimethylstannyl-, a triphenylstannyl-, a dimethylantimonyl-, a diphenylantimonyl, a dimethylbismuthyl-, or a diphenylbismuthyl group. In some embodiments, PAG anions such as these are used for EUV lithography.

The synthesis of the PAGs according to the present disclosure is described exemplary for the 1,2,3,4,5,6-hexacyanoborinine anion:

A solution of 1,2-dihydro-1-rnethoxy-2-(trimethylsilyl) borinine (1.0 g, 5.5 mmol) in pyridine (15 mL) was heated to 60° C. and was maintained at 60° C. for 6 h. The solution turned dark red. After removing volatile components under vacuum, the product was crystallized in THF. The yellow needles thus obtained were washed with pentane and dried under vacuum. 440 mg (52%) pyridine-borinine was obtained.

Pyridine-borinine along with an excess of chlorine was passed through a reaction column with activated carbon pellets. The reaction zone was maintained at 300° C. throughout the reaction. The product subliming from the lower end of the reaction column was hexachloroborinine.

Hexachloroborinine (10 g) and trimethylsilyl cyanide (11 g, 6 eq) were dissolved in 200 mL dimethylformamide at 80° C. for 1.5 h. After cooling, the deep red solution was stirred in 1 L cold water for 12 h. The resulting precipitate was washed with cold water. The thus obtained compound was 1,2,3,4,5,6-hexacyanoborinine. 1,2,3,4,5,6-Hexacyanoborinine was deprotonated to obtain the 1,2,3,4,5,6-hexacyanoborinine anion.

The PAGs disclosed herein can be formulated in chemically amplified photoresist compositions. These chemically amplified photoresist compositions may be used in lithographic processes.

In some embodiments, the content of the PAG in the photoresist composition can be about 10 to 50% by weight. However, the content of the PAG may also range from about 10-80% by weight, 5-95% by weight, etc., based on the total weight of the photoresist composition.

The PAGs according to the present disclosure can be capable of undergoing chemical transformations upon exposure of the photoresist composition (e.g., by DUV irradiation or EUV irradiation), whereby a differential in the solubility of the photoresist in the exposed and unexposed regions is created.

In some embodiments, the photoresist compositions can also include a solvent which is capable of dissolving the PAGs. Examples of such solvents may include, but are not limited to, ethers (e.g., tetrahydrofuran), glycol ethers (e.g., 2-methoxyethyl ether (diglyme), ethylene glycol monomethyl ether, propylene glycol monomethyl ether, propylene glycol monomethyl ether acetate (PGMEA), etc.), aromatic hydrocarbons (e.g., toluene, xylene, benzene, etc.) ketones (e.g., methylisobutylketone, 2-heptanone, cycloheptanone, cyclohexanone, etc.), esters (e.g., ethyl lactate, ethoxy ethyl propionate, etc), etc. A solvent system including a suitable mixture of the aforementioned solvents may also be used. The photoresist composition may also include components such as a photosensitizer, a pigment, a filler, an antistatic agent, a flame retardant, a defoaming agent, a light stabilizer, an antioxidant, and/or other additives.

The photoresist composition can be used in lithographic processes to create patterned material layer structures such as metal wiring lines, holes for contacts or vias, insulation sections (e.g., damascene trenches or shallow trench isolation), trenches for capacitor structures, ion implanted semiconductor structures for transistors, etc. as might be used in integrated circuit devices.

Figure 22:
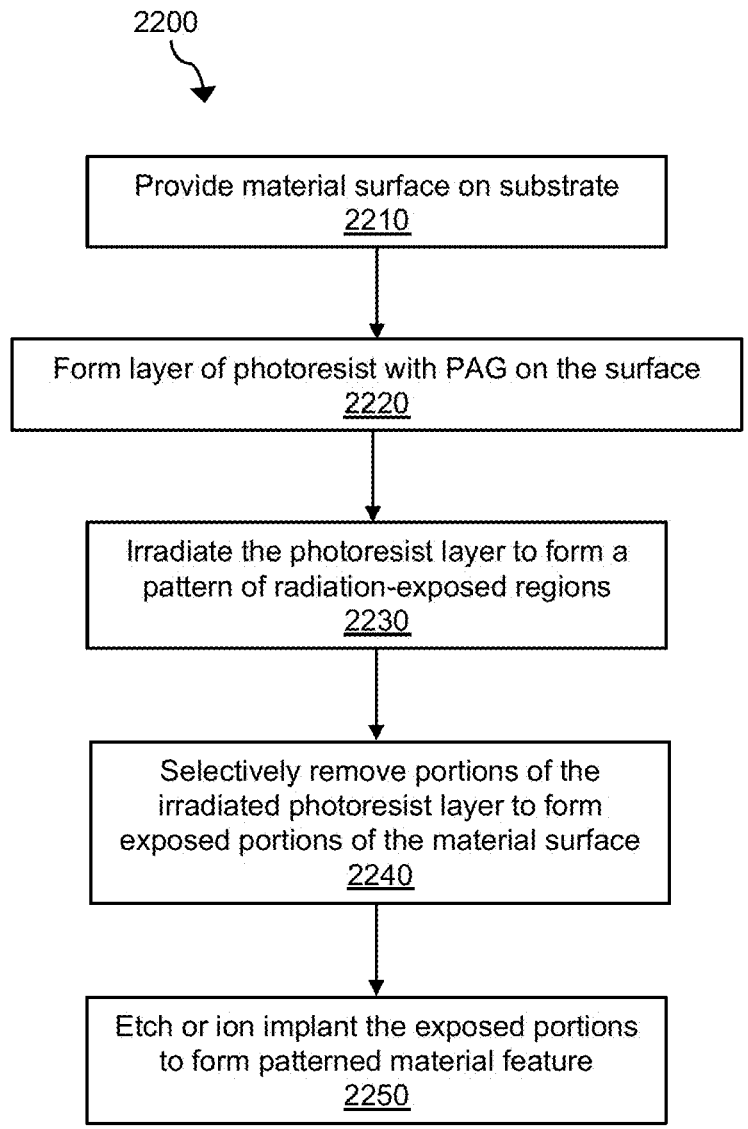
FIG. 22 is a flow diagram illustrating a process of using the photoresist compositions to form patterned material features on a substrate, according to some embodiments of the present disclosure.

FIG. 22 is a flow diagram illustrating a process 2200 of using the photoresist compositions to form patterned material features on a substrate, according to some embodiments of the present disclosure. The substrate may be any substrate conventionally used in processes involving photoresists. For example, the substrate can be silicon, silicon oxide, aluminium, aluminium oxide, gallium arsenide, ceramic, quartz, copper, or any combination thereof, including multilayers.

A material surface is provided on the substrate. This is illustrated at operation 2210. The material surface may have a metal conductor layer, a ceramic insulator layer, a semiconductor layer, or other material depending on the stage of the manufacture process and the desired material set for the end product. A layer of photoresist composition that includes a PAG (e.g., in an amount such as 5 to 95% by weight, 10 to 80% by weight, and 10 to 50% by weight) with a PAG anion disclosed herein (see, e.g., FIGS. 4, 6, 8, 11, 13, and 15) and a cation (e.g., triphenylsulfonium, diphenyliodonium, phenylthiolanium, or derivatives thereof) is formed over the material surface. This is illustrated at operation 2220. The photoresist layer can then be irradiated with an energy ray to form a pattern of radiation-exposed regions. This is illustrated at operation 2230. In some embodiments, the energy ray with which the patternwise irradiation of the photoresist composition is conducted can be a DUV irradiation or an EUV irradiation.

After exposure, the exposed regions of the photoresist layer can be selectively removed to form exposed regions of the material surface. This is illustrated at operation 2240. For example, a structure with the desired pattern can be obtained or developed by contacting the photoresist layer with an aqueous alkaline solution which selectively dissolves the areas of the photoresist which were exposed to radiation in the case of a positive photoresist (or the unexposed areas in the case of a negative photoresist). Some aqueous alkaline solutions or developers have aqueous solutions of tetramethyl ammonium hydroxide. The resulting lithographic structure on the substrate is then typically dried to remove any remaining developer. If a top coat has been used, it can be dissolved by the developer in this step.

The pattern from the photoresist structure can then be transferred to the exposed portions of underlying material of the substrate by etching with a suitable etchant using techniques known in the art. This is illustrated at operation 2250. In some embodiments, the transfer is done by reactive ion etching or by wet etching. Once the desired pattern transfer has taken place, any remaining photoresist may be removed using conventional stripping techniques. Alternatively, the pattern may be transferred by ion implantation to form a pattern of ion implanted material.

What is claimed is:

1. A composition, comprising:
 a photoacid generator (PAG) anion, comprising:
  a first moiety selected from the group consisting of an alkyl group, a monocyclic aromatic group, and a bicyclic aromatic group, wherein the first moiety comprises a carbon atom with a negative elementary charge;
an electron acceptor atom selected from the group consisting of boron(III), aluminum(III), and phosphorus(V), wherein the electron acceptor atom is covalently bonded to the carbon atom; and
R groups comprising at least one electron-withdrawing R group.

2. The composition of claim 1, wherein the PAG anion has the general formula (I):

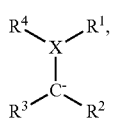

(I)

wherein:
X represents the electron acceptor atom; and
R1, R2, R3, and R4 represent the R groups.

3. The composition of claim 1, wherein the PAG anion has the general formula (II):

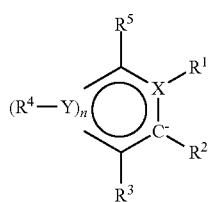

(II)

wherein:
X represents the electron acceptor atom;
R1, R2, R3, R4, and R5 represent the R groups;
Y represents a methylene group; and
n is 0 or an integer in a range from 1 to 3.

4. The composition of claim 3, wherein at least two adjacent groups of the R groups are linked with each other to form a five-, six-, or seven-membered aromatic ring that includes at least one electron-withdrawing group.

5. The composition of claim 1, wherein the PAG anion has the general formula (III):

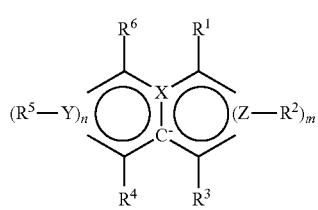

(III)

wherein:
X represents the electron acceptor atom;
R1, R2, R3, R4, R5, and R6 represent the R groups;
Y and Z each represent a methylene group;
n is 0 or an integer in a range from 1 to 3; and
m is 0 or an integer in a range from 1 to 3.

6. The composition of claim 5, wherein at least two adjacent groups of the R groups are linked with each other to form a five-, six-, or seven-membered aromatic ring that includes at least one electron-withdrawing group.

7. The composition of claim 1, wherein the at least one electron-withdrawing R group is selected from the group consisting of cyano, cyanoimino, linear or branched $C_1$ to $C_4$ cyanoalkyl, linear or branched $C_1$ to $C_4$ cyanoalkenyl, linear or branched $C_1$ to $C_4$ cyanoalkylene, $C_1$ to $C_4$ alkylsulfonyl, ($C_1$ to $C_4$ alkylsulfonyl) imino, linear or branched $C_1$ to $C_4$ ($C_1$ to $C_4$ alkylsulfonyl) alkyl, linear or branched $C_1$ to $C_4$ ($C_1$ to $C_4$ alkylsulfonyl) alkenyl, linear or branched $C_1$ to $C_4$ ($C_1$ to $C_4$ alkylsulfonyl) alkylene, fluoro, fluoroimino, linear or branched $C_1$ to $C_8$ fluoroalkyl, (linear or branched $C_1$ to $C_8$ fluoroalkyl) imino, linear or branched $C_1$ to $C_8$ fluoroalkenyl, linear or branched $C_1$ to $C_8$ fluoroalkylene, ($C_1$ to $C_4$ fluoroalkyl) sulfonyl, ($C_1$ to $C_4$ fluoroalkyl) sulfonylimino, linear or branched $C_1$ to $C_4$ ($C_1$ to $C_4$ fluoroalkyl) sulfonylalkyl, linear or branched $C_1$ to $C_4$ ($C_1$ to $C_4$ fluoroalkyl) sulfonylalkenyl, linear or branched $C_1$ to $C_4$ ($C_1$ to $C_4$ fluoroalkyl) sulfonylalkylene, $C_3$ to $C_7$ fluorocycloalkyl, ($C_3$ to $C_7$ fluorocycloalkyl) imino, $C_5$ to $C_7$ fluoroaryl, ($C_5$ to $C_7$ fluoroaryl) imino, and derivatives thereof.

8. The composition of claim 1, wherein the R groups further comprise at least one non-electron-withdrawing R group.

9. The composition of claim 8, wherein the at least one non-electron-withdrawing R group is selected from the group consisting of H, optionally substituted linear or branched alkyl, optionally substituted cycloalkyl, optionally substituted aryl, optionally substituted saturated or unsaturated heterocyclic group, and derivatives thereof.

10. The composition of claim 1, wherein the PAG anion is selected from the group consisting of 2-(dicyanoboranyl)propanedinitrile anion, bis(methylsulfonyl)boranyl-bis(methylsulfonyl)methane anion, dicyanoboranyl-bis(methylsulfonyl)methane anion, 2-(bis(trifluoromethyl)boranyl)-1,1,1,3,3,3-hexafluoropropane anion, bis(trifluoromethylsulfonyl)boranyl-bis(trifluoromethylsulfonyl)methane anion, dicyanoboranyl-bis(trifluoromethylsulfonyl)methane anion, 2-(dicyanoaluminyl)propanedinitrile anion, bis(methylsulfonyl)aluminyl-bis(methylsulfonylmethane) anion, dicyanoaluminyl-bis(methylsulfonylmethane) anion, 2-(bis(trifluoromethyl)aluminyl)-1,1,1,3,3,3-hexafluoropropane anion, bis(trifluoromethylsulfonyl)aluminyl-bis(trifluoromethylsulfonyl)methane anion, dicyanoaluminyl-bis(trifluoromethylsulfonyl)methane anion, bis(cyanoimino)(dicyanomethyl)phosphorane anion, bis(methylsulfonylimino)-bis(methylsulfonyl)methylphosphorane anion, bis(trifluoromethylimino)(1,1,1,3,3,3-hexafluoroprop-2-yl)phosphorane anion, bis(trifluoromethylsulfonylimino)-bis(trifluoromethylsulfonyl)methylphosphorane anion, bis(dicyanomethylene)(dicyanomethyl)phosphorane anion, bis(bis(methylsulfonyl)methylene)-bis(methylsulfonyl)methylphosphorane anion, bis(bis(trifluoromethyl)methylene) (1,1,1,3,3,3-hexafluoroprop-2-yl)phosphorane anion, bis(bis(trifluoromethylsulfonyl)methylene)-bis(trifluoromethylsulfonyl)methylphosphorane anion, 1,2,3,4,5,6-hexacyanoborinine anion, 1,2,3,4,5,6-hexakis(methylsulfonyl)borinine anion, 1-cyano-2,3,4,5,6-pentakis(methylsulfonyl)borinine anion, 1,2,3,4,5,6-hexakis(trifluoromethyl)borinine anion, 1,2,3,4,5,6-hexakis(trifluoromethylsulfonyl)borinine anion, 1-cyano-2,3,4,5,6-pentakis(trifluoromethylsulfonyl)borinine anion, 1,2,3,4,5,6-hexacyanoaluminine anion, 1,2,3,4,5,6-hexakis(methylsulfonyl)aluminine anion, 1-cyano-2,3,4,5,6-pentakis(methylsulfonyl)aluminine anion, 1,2,3,4,5,6-hexakis(trifluoromethyl)aluminine anion, 1,2,3,4,5,6- hexakis(trifluoromethylsulfonyl)aluminine anion, 1-cyano-2,3,4,5,6-pentakis(trifluoromethylsulfonyl)aluminine anion, 1,2,3,4,5,6,7,8-octacyanobenzo[a]borinine anion, 1,8-(1,2,3,4-tetracyanobuta[1,3]dieno)-2,3,4,5,6,7-hexacyanobenzo[a]borinine anion, bis-[1,8:4,5]-(1,2,3,4-tetracyanobuta[1,3]dieno)-2,3,6,7-tetracyanobenzo[a]borinine anion, 1,2,3,4,5,6,7,8-octacyanobenzo[a]aluminine anion, 1,8-(1,2,3,4-tetracyanobuta[1,3]dieno)-2,3,4,5,6,7-hexacyanobenzo[a]aluminine anion, bis-[1,8:4,5]-(1,2,3,4-tetracyanobuta[1,3]dieno)-2,3,6, 7-tetracyanobenzo[a]aluminine anion, 1,2,3,4,5,6-hexakis(methylsulfonyl)borinine anion, 1-cyano-2,3,4,5,6-pentakis(methylsulfonyl)borinine anion, 1,2,3,4,5,6,7,8-octakis(methylsulfonyl)benzo[a]borinine anion, 1,2,3,4,5,6-hexakis(methylsulfonyl)aluminine anion, 1-cyano-2,3,4,5,6-pentakis(methylsulfonyl)aluminine anion, and 1,2,3,4,5,6,7,8-octakis(methylsulfonyl)benzo[a]aluminine anion.

11. The composition of claim 1, wherein the at least one electron-withdrawing R group is selected from the group consisting of a trialkylstannyl-, a triarylstannyl-, a dialkylantimonyl-, a diarylantimonyl, a dialkylbismuthyl-, and a diarylbismuthyl group.

12. The composition of claim 1, wherein the at least one electron-withdrawing R group is selected from the group consisting of cyanoethenyl, dicyanoethenyl, tricyanoethenyl, methylsulfonyl, methylsulfonylimino, cyanomethylene, dicyanomethylene, methylsulfonylmethylene, and bis(methylsulfonyl)methylene.

13. The composition of claim 1, wherein the PAG anion is selected from the group consisting of bis(trimethylstannyldicyanoethen-1-yl)-(1,1,2,4,5,5-hexacyanopent-1,4-dien-3-yl)borane anion, bis(dimethylantimonyldicyanoethen-1-yl)-(1,1,2,4,5,5-hexacyanopent-1,4-dien-3-yl)borane anion, bis(dimethylbismuthyldicyanoethen-1-yl)-(1,1,2,4,5,5-hexacyanopent-1,4-dien-3-yl)borane anion, bis(triphenylstannyldicyanoethen-1-yl)-(1,1,2,4,5,5-hexacyanopent-1,4-dien-3-yl)borane anion, bis(diphenylantimonyldicyanoethen-1-yl)-(1,1,2,4,5,5-hexacyanopent-1,4-dien-3-yl)borane anion, bis(diphenylbismuthyldicyanoethen-1-yl)-(1,1,2,4,5,5-hexacyanopent-1,4-dien-3-yl)borane anion, pentacyano(trimethylstannyl)borinine anion, pentacyano(dimethylantimonyl)borinine anion, pentacyano(dimethylbismuthyl)borinine anion, pentacyano(triphenylstannyl)borinine anion, pentacyano(diphenylantimonyl)borinine anion, pentacyano(diphenylbismuthyl)borinine anion, hexacyano-bis(trimethylstannyl)benzo[a]borinine anion, hexacyano-bis(dimethylantimonyl)benzo[a]borinine anion, hexacyano-bis(dimethylbismuthyl)benzo[a]borinine anion, hexacyano-bis(triphenylstannyl)benzo[a]borinine anion, hexacyano-bis(diphenylantimonyl)benzo[a]borinine anion, and hexacyano-bis(diphenylbismuthyl)benzo[a]borinine anion.

14. The composition of claim 1, wherein a conjugate acid of the PAG anion has a proton dissociation energy smaller than 255 kcal/mol.

15. A photoresist composition comprising a photoacid generator (PAG), wherein the PAG comprises:
a PAG anion, the PAG anion comprising:
a first moiety selected from the group consisting of an alkyl group, a monocyclic aromatic group, and a bicyclic aromatic group, wherein the first moiety comprises a carbon atom with a negative elementary charge;
an electron acceptor atom selected from the group consisting of boron(III), aluminum(III), and phosphorus(V), wherein the electron acceptor atom is covalently bonded to the carbon atom; and
R groups comprising at least one electron-withdrawing R group; and
a cation selected from the group consisting of triphenylsulfonium, diphenyliodonium, phenylthiolanium, and derivatives thereof.

16. The photoresist composition of claim 15, wherein the PAG is in an amount of 5 to 95% by weight.

17. The composition of claim 15, wherein a conjugate acid of the PAG anion has a proton dissociation energy smaller than 255 kcal/mol.

18. A method of forming a patterned material feature on a substrate, comprising:
providing a material surface on the substrate;
forming a layer of a photoresist composition over the material surface, wherein the photoresist composition comprises a photoacid generator (PAG), comprising:
a PAG anion, comprising:
a first moiety selected from the group consisting of an alkyl group, a monocyclic aromatic group, and a bicyclic aromatic group, wherein the first moiety comprises a carbon atom with a negative elementary charge;
an electron acceptor atom selected from the group consisting of boron(III), aluminum(III), and phosphorus(V), wherein the electron acceptor atom is covalently bonded to the carbon atom; and
R groups, wherein at least one of the R groups comprises an electron withdrawing group; and
a cation selected from the group consisting of triphenylsulfonium, diphenyliodonium, phenylthiolanium, and derivatives thereof;
irradiating the photoresist layer with an energy ray to form a pattern of radiation-exposed regions in the photoresist layer;
selectively removing portions of the irradiated photoresist layer to form exposed portions of the material surface; and
etching or ion implanting the exposed portions of the material surface, thereby forming the patterned material feature.

19. The method of claim 18, wherein the energy ray is a deep ultraviolet (DUV) irradiation or an extreme ultraviolet (EUV) irradiation.

20. The method of claim 18, wherein the PAG is in an amount of 5 to 95% by weight.

* * * * *